(12) United States Patent
Kontani et al.

(10) Patent No.: US 7,465,748 B2
(45) Date of Patent: *Dec. 16, 2008

(54) AMIDE DERIVATIVE

(75) Inventors: Toru Kontani, Chuo-ku (JP); Junji Miyata, Chuo-ku (JP); Wataru Hamaguchi, Chuo-ku (JP); Tomoaki Kawano, Chuo-ku (JP); Akio Kamikawa, Chuo-ku (JP); Hiroshi Suzuki, Chuo-ku (JP); Kenji Sudo, Chuo-ku (JP)

(73) Assignees: Astellas Pharma Inc., Tokyo (JP); Rational Drug Design Laboratories, Tokyo (JP)

( * ) Notice: Subject to any disclaimer, the term of this patent is extended or adjusted under 35 U.S.C. 154(b) by 382 days.

This patent is subject to a terminal disclaimer.

(21) Appl. No.: 10/567,565

(22) PCT Filed: Aug. 5, 2004

(86) PCT No.: PCT/JP2004/011573

§ 371 (c)(1), (2), (4) Date: Feb. 8, 2006

(87) PCT Pub. No.: WO2005/014559

PCT Pub. Date: Feb. 17, 2005

(65) Prior Publication Data

US 2006/0229295 A1    Oct. 12, 2006

(30) Foreign Application Priority Data

Aug. 8, 2003    (JP) .............................. 2003-290850

(51) Int. Cl.
*A61K 31/41* (2006.01)
*C07D 271/06* (2006.01)

(52) U.S. Cl. ....................... 514/336; 514/357; 514/364; 514/374; 514/359; 546/336; 546/337; 548/131; 548/215; 548/255

(58) Field of Classification Search ................. 548/131, 548/215, 255; 546/336, 337; 514/357, 336, 514/364, 374, 359
See application file for complete search history.

(56) References Cited

U.S. PATENT DOCUMENTS

| 6,057,451 | A | 5/2000 | Crute et al. |
| 6,458,959 | B1 | 10/2002 | Crute et al. |
| 6,545,055 | B1 | 4/2003 | Zhu et al. |
| 6,638,980 | B1 | 10/2003 | Su et al. |
| 6,903,125 | B2 * | 6/2005 | Kontani et al. .............. 514/364 |
| 2004/0034232 | A1 | 2/2004 | Kontani et al. |

FOREIGN PATENT DOCUMENTS

| WO | WO 97/24343 A1 | 7/1997 |
| WO | WO 00/29399 A1 | 5/2000 |
| WO | WO 02/38554 A1 | 5/2002 |
| WO | WO 03/013531 A1 | 2/2003 |
| WO | WO 03/095435 A1 | 11/2003 |

OTHER PUBLICATIONS

Dr. Richard Hunt, Microbiology and Immunology On-Line at http://pathmicro.med.sc.edu/virol/herpes.htm, downloaded on Apr. 22, 2008.*
International Search Report dated Oct. 13, 2004.
International Search Report dated Nov. 9, 2004.

* cited by examiner

*Primary Examiner*—Kahsay T Habte
(74) *Attorney, Agent, or Firm*—Sughrue Mion, PLLC

(57) ABSTRACT

There is provided a pharmaceutical drug, particularly a novel compound useful for prophylaxis or a therapeutic treatment of various diseases involving infections with viruses of the herpesvirus family, specifically various herpesvirus infections such as varicella (chicken pox) via varicella zoster virus, varicella zoster via recurrent infection with latent varicella zoster virus, herpes labialis and herpes encephalitis via HSV-1 and genital herpes via HSV-2 infection.

An N-{2-[(4-substituted phenyl)amino]-2-oxoethyl}tetrahydro-2H-thiopyran-4-carboxamide derivative, of which phenyl group is substituted at position 4 with a specific 5- or 6-membered heteroaryl group, and a salt thereof have an effective anti-virus activity, and the oral administration thereof at a low dose enabled the therapeutic treatment of the above diseases.

11 Claims, No Drawings

AMIDE DERIVATIVE

FIELD OF THE INVENTION

The present invention relates to a novel amide derivative useful for a pharmaceutical agent, more particularly a prophylaxis and a therapeutic treatment of diseases in which herpesvirus is involved.

BACKGROUND OF THE INVENTION

Viruses belonging to the Herpesviridae family cause various infectious diseases in human and animals. For example, it is known that varicella zoster virus (VZV) causes varicella and herpes zoster, and herpes simplex viruses of types 1 and 2 (HSV-1 and HSV-2) cause infections such as herpes labialis, genital herpes, etc., respectively. In recent years, additionally, infectious diseases caused by herpesviruses such as cytomegalovirus (CMV), EB virus (Epstein-Barr virus; EBV), human herpesviruses 6, 7 and 8, etc. have been elucidated.

Currently, pharmaceutical drugs of nucleic acid series, such as acyclovir (ACV), and its prodrugs, i.e., valacyclovir (VCV), fancyclovir (FCV), etc., are used as drugs against herpesviruses such as VZV and HSV. These pharmaceutical drugs of nucleic acid series are mono-phosphorylated into nucleoside monophosphates by viral thymidine kinase encoded by VZV or HSV and are subsequently converted into triphosphate compounds by cellular enzymes. Finally, the tri-phosphorylated nucleoside analogues are incorporated during the replication of the viral genomes by herpesvirus DNA polymerase, to suppress the extension reaction of the viral DNA chains. Since the reaction mechanism of the existing anti-herpesvirus agents is based on the effect of the "competitive inhibition" toward deoxynucleoside triphosphate, as described above, it is necessary to use these drugs at a high concentration for the exertion of their antiviral effects. Actually, these anti-herpesvirus drugs of nucleic acid series are clinically administered at a dose as high as several hundreds in mg to several grams per day. Since these drugs of nucleic acid series are readily incorporated into the genome DNA of a host via the host DNA polymerase, further, the mutagenicity thereof draws concerns.

On the other hand, lately, several pharmaceutical drugs of non-nucleic acid series and with anti-herpesvirus activity have been reported. For example, there is disclosed an amide or sulfonamide derivative suppressing the HSV helicase-primase enzyme complex to show anti-HSV-1 activity and anti-CMV activity, as represented by the following Formula (G), wherein the N atom is substituted with a thiazolylphenylcarbamoylmethyl group or the like (Patent Reference 1). However, the anti-VZV activity of these compounds is not specifically disclosed therein.

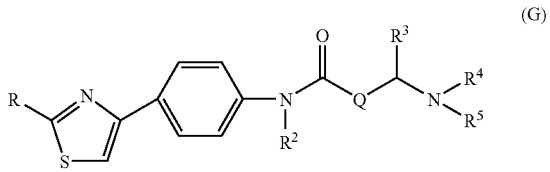

(In the formula, R is hydrogen, a lower alkyl, amino, lower alkylamino or the like; $R^2$ is hydrogen or a lower alkyl, Q may not exist or when it exists, Q represents a methylene; $R^3$ is hydrogen, a lower alkyl or the like; $R^4$ is an unsubstituted or substituted phenyl (lower) alkyl, 1-indanyl, 2-indanyl, (lower cycloalkyl)-(lower alkyl), (Het)-(lower alkyl) or the like; $R^5$ is a phenylsulfonyl, 1- or 2-naphthylsulfonyl, (Het)-sulfonyl, (unsubstituted or substituted phenyl)-Y-$(CH_2)_n$C(O), (Het)-$(CH_2)_n$C(O) or the like, wherein Y is O or S and n is 0, 1 or 2; see the Reference for details.)

Further, there is disclosed an amide or sulfonamide derivative having anti-HSV-1 activity and anti-CMV activity as represented by the following Formula (H) wherein the nitrogen atom is substituted with a thiazolylphenylcarbamoylmethyl group (Patent Reference 2). However, the anti-VZV activity of these compounds is not specifically disclosed therein.

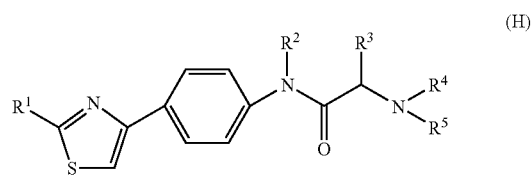

(In the formula, $R^1$ is $NH_2$; $R^2$ is H; $R^3$ is H; $R^4$ is $CH_2Ph$, $CH_2$-(4-pyridyl), $CH_2$-cyclohexyl or the like; and $R^5$ is CO-(substituted phenyl), CO-(unsubstituted or substituted hetero ring) or the like; see the Publication for details.)

The present inventors previously found an amide compound substituted with a thiazolylphenylcarbamoylmethyl group and with favorable anti-VZV activity, as represented by the following formula where the nitrogen atom of the amide group is substituted directly with an aromatic group aryl or heteroaryl group, or the salt thereof. Thus, the inventors filed a patent application (Patent Reference 3).

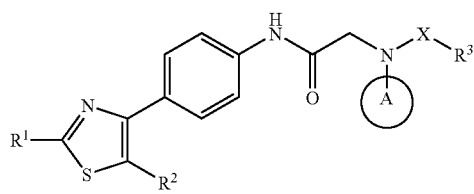

(In the formula $R^1$ and $R^2$ represent —H, -lower alkyl, —NRaRb or the like; A represents -aryl which may have a substituent(s), -heteroaryl which may have a substituent(s) or the like; $R^3$ represents -aryl which may have a substituent(s), -hetero ring which may have a substituent(s) or the like; X represents CO or $SO_2$; see the Publication for details).

[Patent Reference 1] Pamphlet of International Publication WO 97/24343

[Patent Reference 2] Pamphlet of International Publication WO 00/29399

[Patent Reference 3] Pamphlet of International Publication WO 02/38554

Still now, it is strongly desired to create an anti-herpesvirus drug with a satisfactory anti-herpesvirus activity and of non-nucleic acid series, which is highly safe at a low dose and suitable for oral administration.

DISCLOSURE OF THE INVENTION

The inventors carried out intensive studies about a compound having an anti-herpesvirus action. As a result, the inventors found that a novel amide derivative as shown by the following general formula (I), wherein a 1,2,4-oxadiazol-3-yl, 4-oxazolyl, 1,2,3-triazol-2-yl or 2-pyridyl group is introduced as Z in the ring structure in place of the conventional amino-substituted thiazole ring, unexpectedly had a favorable anti-herpesvirus activity. Thus, the invention has been achieved. Compared with the conventional anti-herpesvirus drugs, the compound of the invention has great pharmacokinetics in biological organisms and shows an excellent anti-virus activity when administered orally even at a low dose. Additionally, the compound of the invention draws less mutagenic concerns and has a high safety profile, unlike the pharmaceutical drugs of nucleic acid series.

In other words, the invention relates to a novel amide derivative represented by general formula (I) below or a salt thereof.

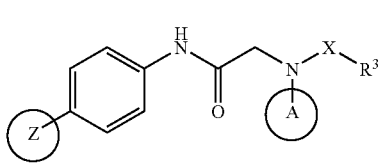

(I)

(In the formula, the symbols represent the following meanings:

Z: 1,2,4-oxadiazol-3-yl, 4-oxazolyl, 1,2,3-triazol-2-yl or 2-pyridyl group,

A: an aryl which may have a substituent(s), heteroaryl which may have a substituent(s), saturated hydrocarbon ring-fused aryl which may have a substituent(s) or saturated heterocyclic ring-fused aryl group which may have a substituent(s), provided that the saturated hydrocarbon ring-fused aryl or saturated heterocyclic ring-fused aryl group is bonded to a nitrogen atom via a carbon atom in an aromatic ring, X: CO or $SO_2$, $R^3$: an alkyl which may have a substituent(s), alkenyl which may have a substituent(s), alkynyl which may have a substituent(s), cycloalkyl which may have a substituent(s), cycloalkenyl which may have a substituent(s), aryl which may have a substituent(s), or heterocyclic group which may have a substituent(s) or $NR_aR_b$, Ra and Rb: which are the same or different from each other, H, a lower alkyl, lower alkenyl, lower alkynyl, cycloalkyl, cycloalkenyl, aryl, 5- or 6-membered monocyclic heteroaryl which has 1 to 4 hetero atoms selected from a group consisting of N, S and O, or lower alkylene-aryl group; the same applies hereinafter.)

Further, the invention relates to a pharmaceutical composition containing an amide derivative represented by general formula (I) and a pharmaceutically acceptable carrier, more specifically to an anti-herpesvirus drug, as well as a therapeutic method for treating diseases in which herpesvirus is involved.

BEST MODE FOR CARRYING OUT THE INVENTION

The amide derivative of general formula (I) according to the invention are to be explained hereinafter.

The term 'lower' in this specification means a straight or branched hydrocarbon chain having 1 to 6 carbon atoms. Examples of the "lower alkyl" groups include preferably an alkyl group having 1 to 4 carbon atoms, particularly preferably a methyl, ethyl, n-propyl, isopropyl, n-butyl, isobutyl and tert-butyl group. Examples of the "lower alkenyl" groups include preferably an alkenyl group having 2 to 5 carbon atoms, particularly preferably a vinyl, allyl, 1-propenyl, isopropenyl, 1-butenyl, 2-butenyl and 3-butenyl group. Examples of the "lower alkynyl" groups include preferably an alkynyl group having 2 to 5 carbon atoms, particularly preferably an ethynyl, 1-propynyl, 2-propynyl, 1-butynyl, 2-butynyl, 3-butynyl and 1-methyl-2-propynyl group. In addition, examples of the "lower alkylene" groups include preferably an alkylene group having 1 to 3 carbon atoms, particularly preferably a methylene, ethylene, trimethylene, propylene and dimethylmethylene group.

Examples of the "alkyl" groups include preferably a straight or branched chain alkyl group having 1 to 10 carbon atoms, more preferably a methyl, ethyl, n-propyl, isopropyl, n-butyl, isobutyl, tert-butyl, 1,1-dimethylpropyl, 2,2-dimethylpropyl, 2,2-diethylpropyl, n-octyl and n-decyl group. Examples of the "alkenyl" and "alkynyl" groups include preferably the straight or branched chain groups having 2 to 10 carbon atoms.

The "aryl" groups mean aromatic hydrocarbon ring groups, preferably an aryl group having 6 to 14 carbon atoms, more preferably a phenyl and naphthyl group. Examples of the "cycloalkyl" groups include a cycloalkyl group having 3 to 10 carbon atoms that may be crosslinked, preferably a cyclopropyl, cyclopentyl, cyclohexyl, cycloheptyl and adamantyl group. Examples of the "cycloalkenyl" groups include preferably a cycloalkenyl group having 3 to 10 carbon atoms, particularly preferably cyclopentenyl and cyclohexenyl group. Examples of the "saturated hydrocarbon ring-fused aryl" groups include preferably a condensed ring group between a benzene ring or naphthalene ring and a $C_{5-6}$ saturated hydrocarbon ring, preferably an indanyl and tetrahydronaphthyl group.

Examples of the "heterocyclic group" include a saturated or unsaturated 5- to 8-membered heterocyclic group which has 1 to 4 hetero atoms selected from N, S and O, and which may be a monocyclic ring, or may form a bicyclic or tricyclic fused ring by being fused with a hetero ring(s) or a hydrocarbon ring(s). They are preferably "heteroaryl", "5- to 8-membered saturated heterocyclic group" and "saturated heterocyclic ring-fused aryl".

The "heteroaryl" preferably include a 5- or 6-membered monocyclic heteroaryl group having 1 to 4 hetero atoms selected from N, S and O and a bicyclic or tricyclic heteroaryl group formed by fusing of the monocyclic heteroaryl group with benzene or heteroaryl ring(s). Examples of monocyclic heteroaryl group preferably include a furyl, thienyl, pyrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidinyl, pyridazinyl, pyrazinyl and triazinyl group, and examples of bicyclic or tricyclic heteroaryl groups preferably include a benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, imidazopyridyl, indolidinyl, carbazolyl, dibenzofuranyl and dibenzothienyl group.

The "5- to 8-membered saturated heterocyclic group" are 5- to 8-membered saturated heterocyclic group which have 1 to 4 hetero atoms selected from N, S and O and may be crosslinked. Examples thereof preferably include a tetrahydro-2H-pyranyl, tetrahydro-2H-thiopyranyl, thiepanyl, thiocanyl, thiabicyclo[3.1.0]hexanyl, perhydro-1,3-thiazinyl, pyrrolidinyl, imidazolidinyl, pyrazolidinyl, piperadinyl, azepanyl, diazepanyl, piperidinyl, morpholinyl and thiomorpholinyl group. More preferred examples are 5- to 7-membered heterocyclic groups. In addition, the "nitrogen-containing saturated heterocyclic group" are the groups having at least one cyclic nitrogen atom among the above "5- to 8-membered saturated heterocyclic group". Examples thereof preferably include a piperidino, morpholino, 1-piperadinyl and 1-pyrolidinyl group.

The "saturated heterocyclic ring-fused aryl" groups include a fused ring groups formed by fusing of the above 5- to 8-membered saturated heterocyclic ring with a benzene ring or naphthalene ring. Preferable examples thereof include 3,4-dihydro-2H-1,4-benzoxadinyl, 3,4-dihydro-2H-1,4-benzothiadinyl, 1,3-benzodioxolyl, 2,3-dihydro-1,4-benzodioxinyl, chromanyl, isochromanyl, 3,4-dihydro-2H-1-benzothiopyranyl, 3,4-dihydro-1H-2-benzothiopyranyl, indolinyl, isoindolinyl, 1,2,3,4-tetrahydroquinolyl and 1,2,3,4-tetrahydroisoquinolyl.

When Ring A is the "saturated hydrocarbon ring-fused aryl" or "saturated heterocyclic ring-fused aryl" group, it is bonded to a nitrogen atom of an amide group via a carbon atom in an aromatic ring.

In accordance with the invention, examples of the "halogen" atoms include F, Cl, Br and I atoms. The "halogeno lower-alkyl" groups are the above lower alkyl groups substituted with one or more of these halogen atoms, preferably $CF_3$.

Substituents for "an alkyl group which may have a substituent(s)", "alkenyl group which may have a substituent(s)" and "alkynyl group which may have a substituent(s)" are preferably 1 to 4 substituents selected from the following Group C.

Group C: a cycloalkyl, cycloalkenyl, aryl, NRaRb, NRc-NRaRb, (nitrogen-containing saturated heterocyclic group which may have a substituent(s) selected from a lower alkyl, lower alkylene COORa and NRaRb group), NRc-(nitrogen-containing saturated heterocyclic group which may have a substituent(s) selected from a lower alkyl, lower-alkylene-COORa and NRaRb group), NRc-lower alkylene-ORa, NRc-lower alkylene-NRaRb, NRc-lower alkylene-(nitrogen-containing saturated heterocyclic group which may have a substituent(s) selected from a lower alkyl, lower alkylene-COORa and NRaRb group), O-lower alkylene-NRaRb, O-lower alkylene-(nitrogen-containing saturated heterocyclic group which may have a substituent(s) selected from a lower alkyl, lower alkylene-COORa and NRaRb group), O-lower alkylene-ORa, O-lower alkyl-COORa, COORa, halogen atoms, CORa, $NO_2$, CN, ORa, O-(halogeno lower alkyl), SRa, SORa, $SO_2Ra$, CO—NRaRb, CO-(nitrogen-containing saturated heterocyclic group which may have a substituent(s) selected from a lower alkyl, lower alkylene-COORa and NRaRb group), NRa—CORb, $SO_2NRaRb$, and =O(oxo) group (wherein Ra and Rb are as described above, and Rc represents H or a lower alkyl group).

Substituents for "cycloalkyl group which may have a substituent(s)", "cycloalkenyl group which may have a substituent(s)", "aryl group which may have a substituent(s)", "heteroaryl which may have a substituent(s)", "saturated hydrocarbon ring-fused aryl which may have a substituent(s)", "saturated heterocyclic ring-fused aryl which may have a substituent(s)", and "heterocyclic group which may have a substituent(s)" are preferably 1 to 5 substituents selected from the following Group D:

Group D: [a lower alkyl group which may have 1 to 3 substituent(s) selected from ORa, SRa, CN, COORa, CONRa, NRaRb and (a nitrogen-containing saturated heterocyclic group which may have a substituent(s) selected from lower alkyl, lower alkylene-COORa and NRaRb)], lower alkenyl, lower alkynyl, halogeno lower alkyl, 5- or 6-membered monocyclic heteroaryl, and the substituents described in the above Group C:

More preferable substituents of the above are 1 to 5 groups selected from Group D1 below:

Group D1: lower alkyl, phenyl, halogeno lower alkyl, COOH, COO-lower alkyl, CO-lower alkyl, halogen atoms, $NO_2$, CN, OH, lower alkylene-OH, lower alkylene-O-lower alkyl, O-lower alkyl, O-halogeno lower alkyl, O-lower alkylene-OH, O-lower alkylene-O-lower alkyl, O-lower alkylene-COOH, O-lower alkylene-COO-lower alkyl, O-lower alkylene-$NH_2$, O-lower alkylene-NH-lower alkyl, O-lower alkylene-N(lower alkyl)$_2$, O-lower alkylene-(a nitrogen-containing saturated heterocyclic group which may be substituted with a lower alkyl group(s)), O-phenyl, O-lower alkylene-phenyl, $NH_2$, NH-lower alkyl, NH-lower alkylene-OH, NH-lower alkylene-O-lower alkyl, NH-lower alkylene-$NH_2$, NH-lower alkylene-NH-lower alkyl, NH-lower alkylene-N(lower alkyl)$_2$, NH-lower alkylene-(a nitrogen-containing saturated heterocyclic group which may be substituted with a lower alkyl group(s)), N(lower alkyl)$_2$, (a nitrogen-containing saturated heterocyclic group which may have a substituent(s) selected from lower alkyl and lower alkylene-COORa), NHCO-lower alkyl, N(lower alkyl)CO-lower alkyl, $CONH_2$, CONH-lower alkyl, CON(lower alkyl)$_2$, =O(oxo), SH, S-lower alkyl, SO-lower alkyl, and $SO_2$-lower alkyl.

In a compound containing a saturated heterocyclic ring having a sulfur atom, the sulfur atom of the ring may form oxide(SO), or dioxide ($SO_2$).

Preferred compounds belonging to Compound (I) of the invention are shown below.

(1) Compounds wherein A is an aryl which may have 1 to 5 substituents selected from Group D, heteroaryl which may have 1 to 5 substituents selected from Group D, saturated hydrocarbon ring-fused aryl which may have 1 to 5 substituents selected from Group D or saturated heterocyclic ring-fused aryl group which may have 1 to 5 substituents selected from Group D; and $R^3$ is a cycloalkyl which may have 1 to 5 substituents selected from Group D, cycloalkenyl which may have 1 to 5 substituents selected from Group D, aryl which may have 1 to 5 substituents selected from Group D, saturated heterocyclic ring-fused aryl which may have 1 to 5 substituents selected from Group D, heteroaryl which may have 1 to 5 substituents selected from Group D, or 5- to 8-membered monocyclic saturated heterocyclic group which may have 1 to 5 substituents selected from Group D.

(2) Compounds wherein X is CO.

(3) Compounds wherein A is an aryl group selected from a phenyl and naphthyl group; a heteroaryl group selected from a pyridyl, pyrimidinyl, benzofuranyl, benzothienyl, benzothiadiazolyl, benzothiazolyl, benzoxazolyl, benzoxadiazolyl, benzimidazolyl, indolyl, isoindolyl, indazolyl, imidazopyridyl and indolidinyl group; a saturated hydrocarbon ring-fused aryl group selected from 4-indanyl, 5-indanyl, 5,6,7,8-tetrahydronaphthalene-1-yl and 5,6,7,8-tetrahydronaphthalene-2-yl; or a saturated heterocyclic ring-fused aryl group selected from a 3,4-dihydro-2H-1,4-benzoxadinyl, 3,4-dihydro-2H-1,4-benzothiadinyl, 1,3-benzodioxolyl, 2,3-dihydro-1,4-benzodioxynyl, chromanyl, isochromanyl, 3,4-dihydro-2H-1-benzothiopyranyl, 3,4-dihydro-1H-2-benzothiopyranyl, indolinyl, isoindolinyl, 1,2,3,4-tetrahydroquinolyl, and 1,2,3,4-tetrahydroisoquinolyl group; the aryl, heteroaryl, saturated hydrocarbon ring-fused aryl and saturated heterocyclic ring-fused aryl each may have 1 to 5 substituents selected from Group D1; $R^3$ is a cycloalkyl selected from cyclopentyl, cyclohexyl and cycloheptyl, cycloalkenyl selected from cyclopentenyl and cyclohexenyl, aryl selected from phenyl and naphthyl, saturated heterocyclic ring-fused aryl selected from 1,3-benzodioxolyl, 2,3-dihydro-1,4-benzodioxinyl, 3,4-dihydro-2H-1-benzothiopyranyl and 3,4-dihydro-1H-2-benzothiopyranyl, heteroaryl selected from pyridyl, pyrimidinyl, benzofuranyl, benzothienyl, benzothiadiazolyl, benzothiazolyl, benzoxazolyl, benzoxadiazolyl, benzimidazolyl, indolyl, isoindolyl, indazolyl, imidazopyridyl and indolidinyl group, or 5- to 8-membered saturated heterocyclic group selected from tetrahydro-2H-pyranyl, tetrahydro-2H-thiopyranyl, thiepanyl, thiocanyl, thiabicyclo[3.1.0]hexanyl, perhydro-1,3-thiazinyl, pyrrolidinyl, imidazolidinyl, pyrazolidinyl, piperadinyl, azepanyl, diazepanyl, piperidinyl, morpholinyl and thiomorpholinyl group, the cycloalkyl, cycloalkenyl, aryl, saturated heterocyclic ring-fused aryl, heteroaryl and 5- to 8-membered saturated heterocyclic group each may have 1 to 5 substituents selected from Group D1 and the sulfur atom of the ring may form oxide or dioxide.

(4) Compounds wherein A is a group selected from a phenyl, pyridyl, benzothiazolyl, indazolyl, 5-indanyl, 1,3-benzodioxolyl and indolinyl group, all of which may have 1 to 3 substituents selected from a group consisting of a lower alkyl, lower alkylene-O-lower alkyl, $CF_3$, halogen atoms, CO-lower alkyl, OH, O-lower alkyl, CN, $OCF_3$, O-lower alkylene-OH, O-lower alkylene-O-lower alkyl, $NH_2$, NH-lower alkyl, N(lower alkyl)$_2$, NH-lower alkylene-OH, NH-lower alkylene-O-lower alkyl and O-lower alkylene-phenyl; and $R^3$ is a group selected from a cyclohexyl, phenyl, naphthyl, pyridyl, pyrimidinyl, benzothiazolyl, benzoxadiazolyl, thiabicyclo[3.1.0]hexanyl, tetrahydro-2H-pyranyl, thiomorpholinyl, tetrahydro-2H-thiopyranyl and perhydro-1,3-thiazinyl group, all of which may be substituted with 1 or 2 substituents selected from halogen atoms, CN, =O, OH, O-lower alkyl, lower alkylene-OH and $CONH_2$ and the sulfur atom of the ring may form oxide or dioxide.

(5) Compounds wherein A is a group selected from a phenyl, benzothiazolyl, indolinyl, 5-indanyl and 1,3-benzodioxolyl group, all of which may have 1 to 3 substituents selected from a group consisting of a lower alkyl, lower alkylene-O-lower alkyl, $CF_3$, halogen atoms, O-lower alkyl, CN, O—$CF_3$, O-lower alkylene-OH, O-lower alkylene-O-lower alkyl, $NH_2$, NH-lower alkylene-OH and NH-lower alkylene-O-lower alkyl.

(6) $R^3$ is a group selected from a cyclohexyl, phenyl, naphthyl, benzoxadiazolyl, thiabicyclo[3.1.0]hexanyl, tetrahydro-2H-pyranyl, thiomorpholinyl, tetrahydro-2H-thiopyranyl and perhydro-1,3-thiazinyl group, which may be substituted with 1 or 2 substituents selected from a group consisting of halogen atoms, CN, =O, OH and O-lower alkyl and the sulfur atom of the ring may form oxide or dioxide;

(6) Compounds wherein Z is 1,2,3-triazol-2-yl group.

(7) Compounds wherein Z is 1,2,4-oxadiazol-3-yl group.

(8) Compounds wherein Z is 4-oxazolyl group.

(9) Compounds wherein A is a group selected from a phenyl and 5-indanyl group, all of which may have 1 to 5 substituents selected from a group consisting of a lower alkyl, O-lower alkyl and halogen atoms; X is CO; and $R^3$ is 1,1-dioxidotetrahydro-2H-thiopyran-4-yl.

(10) Compounds wherein A is a phenyl, which is substituted a methyl group and may further have 1 or 2 substituents selected from a group consisting of methyl and halogen atoms.

(11) Compounds wherein A is 5-indanyl group.

(12) Compounds selected from N-(2,6-dimethylphenyl)-N-(2-{[4-(1,3-oxazol-4-yl)phenyl]amino)-2-oxoethyl)tetrahydro-2H-thiopyran-4-carboxamide 1,1-dioxide; N-(4-methylphenyl)-N-(2-{[4-(1,3-oxazol-4-yl)phenyl]amino)-2-oxoethyl)tetrahydro-2H-thiopyran-4-carboxamide 1,1-dioxide; N-(3-methylphenyl)-N-(2-{[4-(1,3-oxazol-4-yl)phenyl]amino}-2-oxoethyl)tetrahydro-2H-thiopyran-4-carboxamide 1,1-dioxide; N-(2-methylphenyl)-N-(2-([4-(1,3-oxazol-4-yl)phenyl]amino}-2'-oxoethyl)tetrahydro-2H-thiopyran-4-carboxamide 1,1-dioxide; N-(2,4-dimethylphenyl)-N-(2-{[4-(1,3-oxazol-4-yl)phenyl]amino}-2-oxoethyl)tetrahydro-2H-thiopyran-4-carboxamide 1,1-dioxide; N-(3,4-dimethylphenyl)-N-(2-{[4-(1,3-oxazol-4-yl)phenyl]amino}-2-oxoethyl)tetrahydro-2H-thiopyran-4-carboxamide 1,1-dioxide; N-(2,3-dihydro-1H-inden-5-yl)-N-(2-{[4-(1,3-oxazol-4-yl)phenyl]amino)-2-oxoethyl)tetrahydro-2H-thiopyran-4-carboxamide 1,1-dioxide; N-(4-chloro-3-methylphenyl)-N-(2-([4-(1,3-oxazol-4-yl)phenyl] amino)-2-oxoethyl)tetrahydro-2H-thiopyran-4-carboxamide 1,1-dioxide; N-(3-fluoro-4-methylphenyl)-N-(2-{[4-(1,3-oxazol-4-yl)phenyl]amino)-2-oxoethyl)tetrahydro-2H-thiopyran-4-carboxamide 1,1-dioxide; N-(3-fluoro-2,4-dimethylphenyl)-N-(2-([4-(1,3-oxazol-4-yl)phenyl]amino}-2-oxoethyl)tetrahydro-2H-thiopyran-4-carboxamide 1,1-dioxide; N-(3,5-difluoro-4-methylphenyl)-N-(2-([4-(1,3-oxazol-4-yl)phenyl]amino)-2-oxoethyl)tetrahydro-2H-thiopyran-4-carboxamide 1,1-dioxide; N-(2-fluoro-4-methylphenyl)-N-(2-{[4-(1,3-oxazol-4-yl)phenyl]amino}-2-oxoethyl)tetrahydro-2H-thiopyran-4-carboxamide 1,1-dioxide; N-(2,3-dimethylphenyl)-N-(2-([4-(1,2,4-oxadiazol-3-yl)phenyl]amino}-2-oxoethyl)tetrahydro-2H-thiopyran-4-carboxamide 1,1-dioxide; N-(2,4-dimethylphenyl)-N-(2-([4-(1,2,4-oxadiazol-3-yl)phenyl]amino)-2-oxoethyl) tetrahydro-2H-thiopyran-4-carboxamide 1,1-dioxide; N-(2,6-dimethylphenyl)-N-(2-([4-<(1,2,4-oxadiazol-3-yl)phenyl] amino}-2-oxoethyl)tetrahydro-2H-thiopyran-4-carboxamide 1,1-dioxide; N-(4-fluoro-2,6-dimethylphenyl)-N-(2-{[4-(1,2,4-oxadiazol-3-yl)phenyl]amino)-2-oxoethyl) tetrahydro-2H-thiopyran-4-carboxamide 1,1-dioxide; N-(2,3-dihydro-1H-inden-5-yl)-N-(2-{[4-(1,2,4-oxadiazol-3-yl) phenyl]amino}-2-oxoethyl)tetrahydro-2H-thiopyran-4-carboxamide 1,1-dioxide; N-(3-fluoro-4-methylphenyl)-N-(2-{[4-(1,2,4-oxadiazol-3-yl)phenyl]amino}-2-oxoethyl) tetrahydro-2H-thiopyran-4-carboxamide 1,1-dioxide; N-(4-chloro-3-methylphenyl)-N-(2-{[4-(1,2,4-oxadiazol-3-yl) phenyl]amino)-2-oxoethyl)tetrahydro-2H-thiopyran-4-carboxamide 1,1-dioxide; and N-(3-fluoro-2,4-dimethylphenyl)-N-(2-([4-(1,2,4-oxadiazol-3-yl)phenyl] amino}-2-oxoethyl)tetrahydro-2H-thiopyran-4-carboxamide 1,1-dioxide.

The compound of the present invention may form a salt, depending on the kinds of substituent groups. The salts of the compounds of the present invention are those pharmaceutically acceptable. As the acid addition salts, specific examples thereof include those with inorganic acids such as hydrochloric acid, hydrobromic acid, hydroiodic acid, sulfuric acid, nitric acid, phosphoric acid, etc.; or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid, etc. In addition, as a salt with a base, examples thereof include salts with inorganic bases containing metals such as sodium, potassium, magnesium, calcium, aluminum, etc. or with organic bases such as methylamine, ethylamine, ethanolamine, lysine, ornithine, etc., and ammonium salts, and the like.

The compound of the invention encompasses various isomers depending on the kind of the substituent. For example, when there exist geometrical isomers such as cis-trans, etc. and tautomers such as keto-enol, etc., these isomers isolated or mixtures thereof are included in the present invention. Further, the invention's compound sometimes has an asymmetric carbon and isomers based on this asymmetric carbon atom can exist. The invention includes these isomers isolated or mixtures thereof. Furthermore, depending on the kind of the constituent, the invention's compound may form an N-oxide. These N-oxides are also included. Moreover, various hydrates, solvates and polymorphic substances thereof are included. The invention also encompasses all the compounds metabolized in a living body and converted to the invention's compounds or salts thereof, i.e., what is called prodrugs. Examples of the groups which form such prodrugs include those described in Prog. Med. 5: 2157-2161 (1985) and those described in "Drug Design", 163-198 in "Pharmaceutical Research and Development", Vol. 7, published by Hirokawa Publishing Co. in 1990.

Typical methods for producing the compound of the invention are described below.

In the following production methods, it is sometimes effective from the viewpoint of the production technique to replace a certain functional group depending on the type with an appropriate protective group, namely a group readily convertible to the functional group, at the stage of a raw material or intermediate. Afterwards, the protective group can be eliminated, if necessary, to obtain the desired compound. Examples of such a functional group includes an amino group, hydroxyl group, carboxyl group and the like. Protective groups thereof are, for example, those described in Protective Groups in Organic Synthesis, the third edition (T. W. Green and P. G. M. Wuts, eds., JOHN WILLY & SONS, INC.). These may be appropriately used depending on the reaction conditions. For introducing and eliminating such protective groups, the methods described in the reference can be suitably applied.

First Production Method

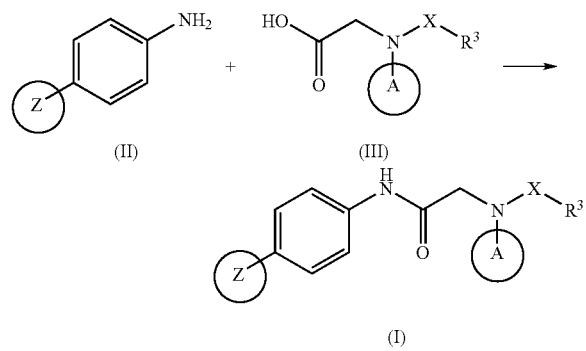

Compound (I) can be easily produced by subjecting Carboxylic Acid Compound (III) and Aniline Derivative (II) to an amidation reaction.

The amidation reaction can be carried out by general methods. For example, the method described in "Courses in Experimental Chemistry" edited by the Chemical Society of Japan, the fourth edition (Maruzen), Vol. 22, pp. 137-173 may be applicable. Preferably, the reaction is carried out by converting Carboxylic Acid Compound (III) to a reactive derivative such as an acid halide (acid chloride, etc.) or an acid anhydride, and then reacting the resulting reactive derivative with Aniline Derivative (II). In the case of using a reactive derivative of carboxylic acid, a base [an inorganic base such as potassium carbonate, sodium hydroxide, etc. or an organic base such as triethylamine (TEA), diisopropylethylamine, pyridine, etc.] is preferably added. In addition, the amidation reaction may be carried out by reacting carboxylic acid in the presence of a condensation agent [1-ethyl-3-(3-dimethylaminopropyl)carbodiimide (WSC), 1,1'-carbonylbis-1H-imidazole (CDI), etc.]. In this case, additives such as 1-hydroxybenzotriazole (HOBt), etc. may be added. The reaction temperature can be appropriately selected depending on the raw material compound used. The solvent usable includes those inert to the reaction, for example, aromatic hydrocarbon-series solvents such as benzene, toluene, etc.; ether-series solvents such as tetrahydrofuran (THF), 1,4-dioxane, etc.; halogenated hydrocarbon-series solvents such as dichloromethane, chloroform, etc.; amide-series solvents such as N,N-dimethylformamide (DMF), N,N-dimethylacetamide, etc.; basic solvents such as pyridine, etc.; and the like. The solvent is appropriately selected depending on the type of the raw material compound and the like, and can be used alone or as a mixture of two or more of them.

Second Production Method

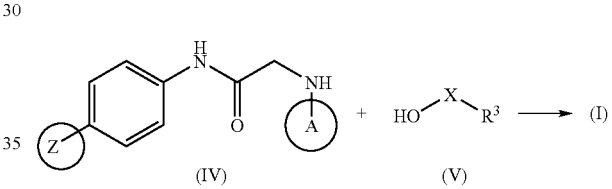

Compound (I) is obtained by subjecting an amine compound represented by general formula (IV) and carboxylic acid or Sulfonic Acid Compound (V) to an amidation reaction or sulfonamidation reaction.

The amidation can be carried out in the same manner as in the first method.

The sulfonamidation reaction can be carried out according to a usual method by reacting Amine Compound (IV) with a reactive derivative of sulfonic acid of Compound (V). Examples of a reactive derivative of sulfonic acid include acid halides (acid chloride, acid bromide, etc.), acid anhydrides (sulfonic acid anhydride prepared from two molecules of sulfonic acid), acid azides and the like. Such a reactive derivative of sulfonic acid can be easily obtained from a corresponding sulfonic acid according to a method generally used. When an acid halide is used as the reactive derivative, the reaction is preferably carried out in the presence of a base (inorganic bases such as sodium hydroxide, sodium hydride, etc. or organic bases such as pyridine, TEA, diisopropylethylamine, etc.). In the case of using such a reactive derivative as an acid anhydride, acid azide, etc., the reaction can be carried out in the absence of a base. In some cases, the reaction may be carried out in the presence of an inorganic base such as sodium hydride, etc. or an organic base such as TEA, pyridine, 2,6-lutidine, etc. The reaction temperature is appropriately selected depending on the kind of the sulfonic acid reactive derivative and the like. As a solvent, solvents inert to the reaction, for example, those exemplified for amidation in the above first method can be employed.

In addition, depending on the kind of the substituent, the desired Compound (I) can be prepared by subjecting to a substituent modification reaction, which is well known by those skilled in the art. For example, known reactions such as the aforementioned amidation, sulfonamidation, N-alkylation described in "Courses in Experimental Chemistry" edited by the Chemical Society of Japan (Maruzen), and the like can be suitably applied. The order of the reactions may be altered depending on the compound desired and the kind of the reaction applied.

The aforementioned raw material compounds can be easily produced using known reactions, e.g., those described in "Courses in Experimental Chemistry" edited by the Chemical Society of Japan (Maruzen), in the pamphlet of the International Publication WO 02/38554, and the like. The typical production methods thereof are described below.

Production Method of Compound (III)

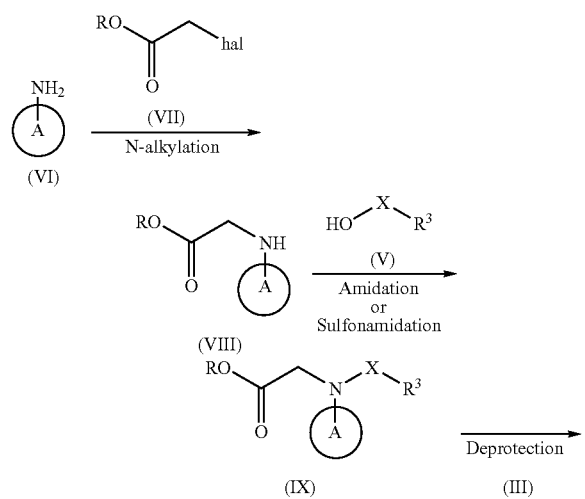

Production Method of Compound (IV)

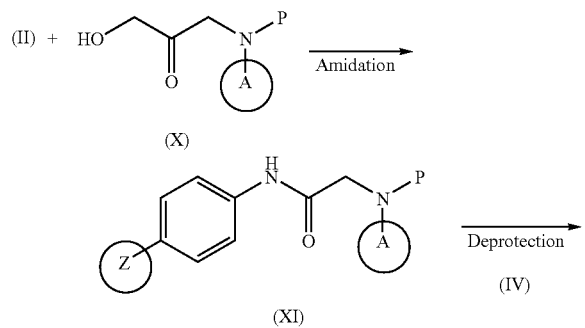

(In the formula, R means a group capable of forming an ester residue, such as a lower alkyl group, aralkyl group, etc.; and P means a protective group of an amino group, such as a fluorenylmethoxycarbonyl (Fmoc) group, etc.)

In the reaction scheme above, amidation can be carried out in the same manner as in the above first production method, and sulfonamidation in the same manner as in the second production method.

N-alkylation of Compound (VI) can be carried out using Halogenated Alkyl Compound (VII) according to usual methods, e.g., the method described in the aforementioned "Courses in Experimental Chemistry", the fourth edition (Maruzen), Vol. 20, pp. 279-318. The reaction can be carried out under the temperature of from cooling to heating. Examples of the solvent usable include solvents inert to the reaction, for example, those exemplified for the amidation in the first production method, etc. The reaction is carried out preferably in the presence of a base such as potassium carbonate, sodium hydroxide, sodium hydride, etc. Herein, the amidation may be first carried out and subsequently, the N-alkylation may be carried out.

Deprotection for obtaining Carboxylic Acid Compound (III) can be carried out by appropriately applying a general method depending on the ester type. In the case of alkyl esters such as an ethyl ester, etc., the deprotection can be preferably carried out by treating them with a base such as sodium hydroxide aqueous solution, etc. In the case of aralkyl esters such as a benzyl ester, etc., the deprotection can be carried out by reducing them with palladium-carbon (Pd—C) under hydrogen atmosphere. The reactions can be carried out according to the method described in the aforementioned "Protective Groups in Organic Synthesis", the third edition.

Deprotection for obtaining Amine Compound (IV) is carried out by appropriately applying a general method depending on the type of the protective group. For example, the method described in the aforementioned "Protective Groups in Organic Synthesis", the third edition, pp. 503-572 can be applied.

A desired raw material compound can be produced by subjecting the compound with a certain substituent type to a substituent modification reaction well known to those skilled in the art.

Various isomers can be isolated according to the usual method by utilizing the difference of physicochemical properties among them. For example, a racemic compound can be led to a stereochemically pure isomer by the generally used optical resolution method [e.g., a method of producing a diastereomeric salt with a general optically active acid (tartaric acid, etc.) and subjecting the salt to optical resolution, or other methods]. Further, diastereomer mixtures can be isolated, for example, by fractional crystallization, chromatography or the like, and optically active compounds can be produced by using a suitable optically active raw material.

The compound of the invention obtained in this manner is isolated and purified in its free form or as a salt thereof after a salt formation process by a general method. The isolation and purification are carried out by employing general chemical procedures such as extraction, concentration, evaporation, crystallization, filtration, recrystallization, various chromatographic techniques and the like.

The pharmaceutical composition of the invention, which contains as effective components one type or two or more types of the compound of the invention, can be prepared according toga method usually used by using pharmaceutical carriers, excipients and the like for general use in this field. Administration thereof may be either oral via tablets, pills, capsules, granules, powders, liquids, etc. or parenteral dosing via injections such as intravenous injections, intramuscular injections, etc., external agents such as ointments, plasters, creams, jellies, cataplasm, sprays, lotions, eye drops, eye ointments, etc., suppositories, inhalation agents, and the like.

As the solid composition for oral administration, tablets, powders, granules and the like are used. In such a solid composition, one or more active substances are mixed with at least one inert excipient, for example, lactose, mannitol, glucose, hydroxypropyl cellulose, microcrystalline cellulose, starch, polyvinylpyrrolidone, magnesium metasilicate aluminate, etc. According to general methods, the composition may contain inert additives such as lubricants, e.g., magnesium stearate, etc.; disintegrators, e.g., sodium carboxymethyl starch, etc.; and dissolution auxiliary agents. The tablets or pills may be coated with sugar coating or stomach-soluble or enteric coating.

Examples of the liquid composition for oral administration include pharmaceutically acceptable emulsions, liquids, suspensions, syrups, elixirs, etc., in which inert solvents for general use such as purified water, ethanol, etc. can be incorporated. In addition to the inert solvents, the composition may further contain auxiliary agents such as solubilizing agents, moistening agents and suspending agents; sweetening agents; flavoring agents; aromatic agents and preservatives.

Examples of the injections for parenteral administration include sterile aqueous or non-aqueous liquids, suspensions and emulsions. The aqueous solvents include, for example, distilled water for injections and physiological saline. The non-aqueous solvents include, for example, propylene glycol, polyethylene glycol, vegetable oils such as olive oil, alcohols such as ethanol, Polysorbate 80 (under trade name) and the like. Such compositions may further contain isotonic agents, preservatives, moistening agents, emulsifying agents, dispersing agents, stabilizers and dissolution auxiliary agents. These are sterilized by filtering through bacteria-retaining filters, by incorporating sterilizing agents, or by irradiation. Alternatively, these may be produced into a sterile solid composition and then dissolved or suspended in sterile water or sterile solvents for injections prior to use.

Examples of the external agents include ointments, plasters, creams, jellies, cataplasms, sprays, lotions, eye drops, eye ointments and the like. The external agent contains generally used ointment bases, lotion bases, aqueous or non-aqueous liquids, suspensions, emulsions and the like. As the ointment or lotion bases, polyethylene glycol, propylene glycol, white Vaseline, white beeswax, polyoxyethylene hardened castor oil, glycerin monostearate, stearyl alcohol, cetyl alcohol, lauromacrogol, sorbitan sesquioleate, and the like can be mentioned as examples.

Generally, the suitable daily dose of the compound of the invention is about 0.001 to 50 mg/kg/body weight, preferably 0.01 to 30 mg/kg/body weight, more preferably 0.05 to 10 mg/kg/body weight, for oral administration. For intravenous administration, the daily dose is about 0.0001 to 10 mg/kg/body weight, preferably 0.001 to 1.0 mg/kg/body weight. The dose is administered once or in separate portions per day, and is appropriately determined depending on each case, in terms of the symptom, age, sex and the like. When the compound of the invention is to be used as an external agent, the agent containing the compound of the invention in an amount of 0.0001 to 20%, preferably 0.01 to 10%, is desirable. The external agent is administered locally once or in separate portions per day depending on the symptom.

The compound of the invention may be appropriately used in combination with other pharmaceutical agents. Examples of the agents usable in combination include other anti-herpesvirus agents such as ACV, VCV, FCV, pencyclovir (PCV), vidarabine (ara-A), BVDU (bromovinyldeoxyuridine), foscarnet (PFA), gancyclovir (GCV), etc.; analgesics for neuralgia after varicella zoster, such as amitriptyline (tricyclic antidepression agent), gabapentin (anti-spasm agent), lidocaine and mexiletine (anti-arrhythmia agent), capsicin, etc.; and antiinflammatorial analgesics such as indometacin, ibuprofen, celecoxib, etc.

The effects of the compound of the invention were confirmed by the following pharmacological tests.

Test Example 1

Anti-VZV Activity Assay

This assay was carried out in accordance with the method described by Shigeta S. (The Journal of Infectious Diseases, 147, 3, 576-584 (1983). Specifically, human embryonic fibroblast (HEF) cells were inoculated in a 96-well microtiter plate, using a growth culture medium [Eagle MEM (Nissui) supplemented with 10% (v/v) fetal bovine serum (FBS; Sigma)], for culturing in 5% $CO_2$ at 37° C. for 4 days until a monolayer was formed. After washing the cells with a maintenance medium, the cells were inoculated with 100 µl/well of VZV (strain CaQu) which had been diluted to 20 to 30 pfu/100 µl with the maintenance medium (Eagle MEM supplemented with 2% FBS). The plate was centrifuged at 2,000 rpm for 20 minutes at room temperature and then incubated at 37° C. for 3 hours in an atmosphere of 5% $CO_2$ to infect with VZV. After washing three times with the maintenance medium, 100 µl of each test drug diluted to an appropriate concentration with the maintenance medium was added to each well. After culturing the cells at 37° C. for 3 to 4 days in an atmosphere of 5% $CO_2$, the cells were fixed with 100 µl/well of 10% formalin/PBS for 2 to 3 hours. After the cells were cultured in 5% $CO_2$ at 37° C. for 3 to 4 days, 10% formalin/PBS was added at 100 µl/well to fix the cells for 2 to 3 hours. After discarding the fixing solution and culture supernatant and subsequently washing the plate with water, a staining solution (0.025% Crystal Violet) was added at 50 µl/well for staining for 2 to 3 minutes, and then, the plate was washed with water and dried at 37° C. Cellular death is induced in the HEF cells infected with VZV, so that plaques of the dead cells are formed in the monolayer of the HEF cells. The number of such plaques was counted with a microscope, to calculate the $EC_{50}$ value of the test drug as a concentration to inhibit 50% of the plaques.

Compared with acyclovir with the $EC_{50}$ value of 3.4 µM, the $EC_{50}$ values of the compounds in Examples 1, 11, 13, 27, 37, 39, 98 and 125 of the invention are 0.075, 0.060, 0.033, 0.10, 0.095, 0.082, 0.14 and 0.19 µM in this order. It was verified that the compounds of the Examples had great anti-VZV activity.

Test Example 2

Anti-HSV-1 Activity Assay 10,000 MRC-5 cells were inoculated and cultured in a 96-well microtiter plate, using the growth culture medium [Eagle MEM (Nissui) supplemented with 10% FBS] in 5% $CO_2$ at 37° C. for 4 to 5 days until a monolayer was formed. After the cells were washed with the maintenance culture medium [Eagle MEM supplemented with 2% (v/v) FBS], 100 µl of the maintenance culture medium dissolving therein an appropriate concentration of a test reagent was added to each well. Immediately after the test drug was added, an HSV-1 (strain KOS) solution was inoculated at 50 $TCID_{50}$ (50% tissue culture infectious dose)/100 µl.

After the cells were cultured in 5% $CO_2$ at 37° C. for 5 days, 20 µl of MTT solution [3-(4,5-dimethyl-2-thiazolyl)-2,5-diphenyl-2H-tetrazolium bromide; Sigma] (diluted with PBS to 7.5 mg/ml) was added to each well, for another 24-hour incubation. After the culture medium was discarded, 100 μl of a solvent (prepared by adding 10% Triton X 100 (v/v) and 0.4% hydrochloric acid to isopropanol) was added to each well, to solubilize the generated formazan. The absorbance at 540 nm or 690 nm was measured with a microplate reader. Based on the suppression ratio (%) of the cellular death of the MRC-5 cell via HSV-1 replication, the $EC_{50}$ value of the test drug was calculated.

Compared with acyclovir with the $EC_{50}$ value of 0.48 μM, the $EC_{50}$ values of the compounds of Examples 1, 11, 13, 27, 37, 39, 98 and 125 of the invention are 0.075, 0.040, 0.0060, 0.060, 0.026, 0.029, 0.042 and 0.028 μM in this order. It was verified that the compounds of the Examples had great anti-HSV activity.

Test Example 3

Using a cutaneous HSV-1 infection mouse model prepared in accordance with the method of H. Machida et al. (Antiviral Res., 1992, 17, 133-143), in vivo activity of the compounds of the invention was tested. The skin of each HR-1 hairless mouse [female, 7 weeks of age] was scratched lengthwise and breadthwise several times using a needle and a virus suspension (HSV-1 strain WT-51, $1.5 \times 10^4$ PFU/15 μl) was droped to the scarified region for infection, while anesthetized with diethyl ether Tested compounds were administered orally as a methyl cellulose suspension, except for compounds marked with asterisk which were dissolved in 20% Cremophor EL (Nakarai Tesuku)/20% polyethylene glycol (PEG) 400/60% $H_2O$ solution, starting at 3 hours after the infection, and then at a dose of 10 mg/kg twice a day for 5 days. The symptom of the skin lesion caused by HSV-1 infection were classified in the following scores for 17 days:

Score 0: no signs of infection.
Score 1: localized, barely perceptible small vesicles.
Score 2: slight vesicle spread.
Score 3: large patches of vesicles formed.
Score 4: zosteriform vesicles.
Score 5: large patches of ulcers formed.
Score 6: zosteriform with severe large ulcers.
Score 7: hind limb paralysis or death.

The AUC value was calculated from each group's mean disease score, and the disease inhibitory rate of the group administered with each test compound to the placebo group was calculated using the AUC. The results are shown in Table below.

TABLE 1

| Test compound | Inhibitory activity (%) | Test compound | Inhibitory activity (%) |
|---|---|---|---|
| Example 1 | *93 | Example 14 | 98 |
| Example 6 | 92 | Example 24 | 89 |
| Example 11 | 92 | Example 37 | 100 |
| Example 98 | *95 | Example 125 | *80 |
| Comparative Compound A | 38 | Comparative Compound B | 2 |
| Comparative Compound C | 44 | Comparative Compound D | 43 |

Comparative Compound A:

Compound of Example 49, Reference 3

Comparative Compound B:

Compound of Example 85, Reference 3

Comparative Compound C:

Compound of Example 87, Reference 3

Comparative Compound D:

Compound of Example 119, Reference 3

The inhibition ratio of the lesions in the groups administered with the compound of the invention was high, which verifies that the compound of the invention has greater suppressive activity of the exacerbation of the lesions than the representative compound tested herein, disclosed in Reference 3.

As apparent from the above, it was confirmed that the compounds of the invention orally administered to in vivo animal model groups have good anti-herpesvirus activity at a low dose.

Additionally, the compound which has weak inhibitory activity against CYP enzymes among the compounds of the invention is advantageously useful with little concern about drug-drug interaction with other drugs.

EXAMPLE

Production examples of the compounds of the invention are shown below as Examples. Herein, many of the raw material compounds for use in the following reactions are known in the pamphlet of the International Publication WO 02/38554 and the like, and can therefore be readily available according to the methods described in these known references. Production examples of novel compounds among the raw materials are shown below in Reference Examples.

Reference Example 1

An aqueous sodium carbonate solution and tetrakis triphenylphosphine palladium were added to a DME solution of 3-bromothiophene and 4-(4,4,5,5-tetramethyl-1,3,2-dioxaborolan-2-yl)aniline, and the mixture was refluxed under heating for 6 hours with argon atmosphere. After cooling to room temperature, the reaction mixture was added with ethyl acetate and water to separate an organic layer, which was then washed and dried. The solvent was evaporated under reduced pressure. The resulting crude product was purified by silica gel column chromatography, to obtain 4-(3-thienyl)aniline (pale yellow solid). Electron Impact-MS (M)$^+$: 175.

Reference Example 2

Ethyl cianoformate was added to a dodecane suspension of 5-(4-nitrophenyl)-1,3,4-oxathiazol-2-on, and the mixture was refluxed under heating for 3 hours. After cooling the reaction mixture to room temperature, the precipitation was separated by filtration and washed with hexane. The crude product obtained was purified by silica gel column chromatography to obtain ethyl 3-(4-nitrophenyl)-1,2,4-thiadiazole-5-carboxylate (pale yellow solid). The ethanol suspension of this product was added with water and sodium hydroxide and heated at 85° C. for 40 minutes while stirring. After cooling to room temperature, the mixture was added with 1M hydrochloric acid to make it acidic. The resulting mixture was heated for one hour while stirring on an oil bath at 95° C. The mixture was then cooled to room temperature and added with chloroform and an aqueous sodium hydrogencarbonate to separate an organic layer, which was then washed and dried. The solvent was evaporated under reduced pressure to obtain 3-(4-nitrophenyl)-1,2,4-thiadiazol (pale yellow solid). The ethanol suspension of this product was added with water and 1M hydrochloric acid, heated to 80° C. and added with reduced iron. The reaction mixture was further heated at 80° C. for 50 minutes while stirring and then filtered through Celite. After evaporation of the ethanol in the resulting filtrate under reduced pressure, chloroform and an aqueous sodium hydrogencarbonate were added to the residue to separate an organic layer, which was then washed and dried. The solvent was evaporated under reduced pressure to obtain 4-(1,2,4-thiadiazol-3-yl)aniline (pale yellow solid). Electron Impact-MS (M)$^+$: 177.

Reference Example 3

To an ethanol suspension of 3-(4-nitrophenylyisoxazole, water and 1M hydrochloric acid were added. The mixture was heated to 80° C. and added with iron. After heating the mixture to 80° C. for 40 minutes while stirring, it was filtered through Celite, and the ethanol in the filtrate was evaporated under reduced pressure. The resulting residue was added with chloroform and an aqueous solution of sodium hydrogencarbonate to separate an organic layer, which was washed and dried. By evaporation of the solvent under reduced pressure, 4-isoxazol-3-ylaniline (yellow oily product) was obtained. FAB-MS [(M+H)$^+$]: 161.

Reference Example 4

5% Palladium-carbon powder was added to an ethanol-tetrahydrofuran mixed suspension of 4-(4-nitrophenyl)-1,3-oxazol and stirred for 12 hours at room temperature in a hydrogen atmosphere. The reaction solution was filtered through Celite and the filtrate was evaporated under reduced pressure. The resulting crude product is purified with a silica gel column chromatography to obtain [4-(1,3-oxazol-4-yl)phenyl]amine (pale yellow solid). Electron Impact-MS(M)$^+$: 160.

Reference Example 5

Potassium carboxylate and ethyl bromoacetate were added to a DMF solution of 4-methylaniline and heated while stirring. The reaction mixture was added with water and ethyl acetate. After the organic layer was separated, washed and dried, the solvent was evaporated under reduced pressure to obtain a crude product. The crude product was dissolved in methylene chloride, and pyridine, tetrahydro-2H-thiopyrane-4-carbonyl chloride 1,1-dioxide were added to the resulting solution and stirred. After the reaction solution was concentrated, 1M hydrochloric acid and chloroform were added. The organic layer separated was washed and dried and the solvent was evaporated under reduced pressure. The resulting crude product was purified with a silica gel column chromatography to obtain ethyl ([(1,1-dioxotetrahydro-2H-thiopyran-4-yl)carbonyl](4-methylphenyl)amino)acetate (colorless oily product). FAB-MS [(M+H)$^+$]: 354.

Reference Examples 6 to 30

Compounds of Reference Examples 6 to 30, which are described in Tables 2 and 3 below, were obtained in the same manner as in Reference Example 5.

Example 1

To an ethanol (10 ml) solution of ethyl {(2,6-dimethylphenyl)[(1,1-dioxide tetrahydro-2H-thiopyran-4-yl)carbonyl]amino}acetate (735 mg) was added aqueous 1M sodium hydroxide solution (2.3 mL). The mixture was stirred at room temperature for 5 hours. After 1M hydrochloric acid was added to the reaction mixture to make the solution acidic, water and chloroform were added thereto to separate the organic layer. Further, the organic layer was dried over anhydrous sodium sulfate and filtered, and then, the solvent was evaporated under reduced pressure. After the resulting crude carboxylic acid product was dissolved in chloroform (15 ml), WSC HCl (422 mg) and [4-(1,3-oxazol-4-yl)phenyl]amine (320 mg) were added sequentially to the resulting solution, which was stirred at room temperature for 4 hours. After a saturated sodium hydrogencarbonate solution and chloroform were added to the reaction solution, the organic layer was separated. The organic layer was washed with a saturated sodium chloride solution, dried over anhydrous magnesium sulfate and filtered, from which the solvent was evaporated under reduced pressure. The resulting crude product was rinsed in hexane-ethyl acetate (=3/2), and then recrystallized from ethanol, to obtain N-(2,6-dimethylphenyl)-N-(2-([4-(1, 3-oxazol-4-yl)phenyl]amino)-2-oxoethyl)tetrahydro-2H-thiopyran-4-carboxamide 1,1-dioxide (colorless crystal) in a yield of 610 mg.

Examples 2-125

Compounds of Examples 2 to 125 shown in Tables 4 to 24 below were obtained in the same manner as in Example 1.

The physicochemical properties of the compounds of Reference Examples are shown in Tables 2 and 3, while Tables 4 to 24 show the structures and physicochemical properties of the compounds of Examples.

Tables 25 to 26 show specific examples of other compounds included in the invention. These compounds can be easily produced according to the methods described in the above Examples or Production Methods, or by applying to the methods slight modification well-known by those skilled in the art.

Abbreviations in the tables have the following meanings. Ref: Reference Example; Ex: Example; Co: Compound Number; Str: structural formula; Dat: physico-chemical properties (F+: FAB-MS [(M+H)$^+$]; F–: FAB-MS [(M–H)$^-$] }; ESI+: ESI (electrospray ionization)-MS [(M+H)$^+$]; N1: δ ppm of the characteristic peak in $^1$H-NMR (DMSO-d$_6$, TMS internal standard); Ph: phenyl; Me: methyl; Et: ethyl; Pr: propyl; and Bn: benzyl. Herein, the numerical figure before each substituent group indicates the position for its substitution. For example, 3,4-(Cl)$_2$-5-F-Ph indicates a 3,4-dichloro-5-fluorophenyl group.

INDUSTRIAL APPLICABILITY

Since the compound of the invention has favorable anti-herpesvirus activity and shows an excellent anti-virus activity when administered orally even at a low dose compared with the conventional anti-herpesvirus drugs, it is useful for a pharmaceutical drug, particularly for prophylaxis or a therapeutic treatment of various diseases involving infections with viruses of the herpesvirus family, specifically various herpesvirus infections such as varicella (chicken pox) via varicella zoster virus, varicella zoster via recurrent infection with latent varicella zoster virus, herpes labialis and herpes encephalitis via HSV-1 and genital herpes via HSV-2 infection, as an anti-herpesvirus drugs with high safety profile.

TABLE 2

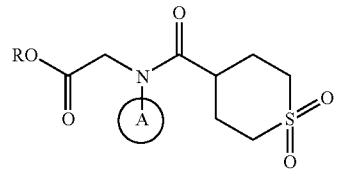

(III)

| Ref | A | R | Dat |
|---|---|---|---|
| 6 | 4-F—Ph | Et | F+: 358 |
| 7 | 4-Me—Ph | Et | F+: 354 |
| 8 | 3-F—Ph | Et | F+: 358 |
| 9 | 3-Me—Ph | Et | F+: 354 |
| 10 | 3,4-F$_2$—Ph | Et | F+: 376 |
| 11 | 2-Me—Ph | Et | F+: 354 |
| 12 | 3,5-(Cl)$_2$—Ph | Et | F+: 408 |
| 13 | 4-Pr—Ph | Et | F+: 382 |
| 14 | 2,3-Me)$_2$—Ph | Et | F+: 368 |
| 15 | 2,4-(Me)$_2$—Ph | Et | F+: 368 |
| 16 | 2,5-(Me)$_2$—Ph | Et | F+: 368 |
| 17 | 2,6-(Me)$_2$—Ph | Et | F+: 368 |
| 18 | 3,4-(Me)$_2$—Ph | Et | F+: 368 |
| 19 | 3,5-(Me)$_2$—Ph | Et | F+: 368 |
| 20 | 2,4,6-(Me)$_3$—Ph | Et | F+: 382 |
| 21 | 4-F-2,6-(Me)$_2$—Ph | Et | F+: 386 |
| 22 | 4-F-3-Me—Ph | Et | F+: 372 |
| 23 | 3-Cl-4-F—Ph | Et | F+: 392 |
| 24 | 3-Br-4-Me—Ph | Et | F+: 433 |
| 25 | 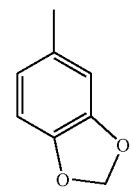 | Et | F+: 384 |
| 26 | 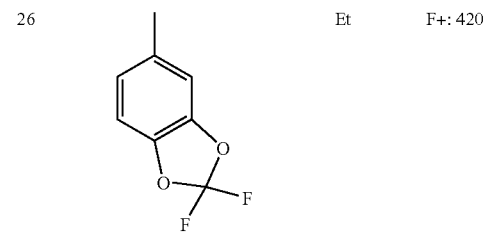 | Et | F+: 420 |

TABLE 3

| Ref | Str | Dat |
|---|---|---|
| 27 | 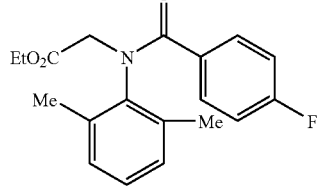 | F+: 330 |

TABLE 3-continued

| Ref | Str | Dat |
|---|---|---|
| 28 | (cyclohexane with CN, N-substituted with EtO2C-CH2- and p-tolyl, C(=O)) | F+: 329 |
| 29 | (tetrahydrothiopyran S-oxide, C(=O)-N(p-tolyl)(CH2CO2Et)) | ESI+: 338 |
| 30 | (tetrahydropyran, C(=O)-N(p-tolyl)(CH2CO2Et)) | F+: 306 |

TABLE 4

(Ia)

| Ex | A | Dat |
|---|---|---|
| 1 | 2,6-(Me)₂—Ph | F+: 482<br>N1: 1.87-2.42(5H, m), 2.13(6H×0.1, s), 2.33(6H×0.9, s), 2.97-3.27(4H, m), 4.19(2H×0.9, s), 4.48(2H×0.1, s), 7.07-7.25(3H, m), 7.62-7.66(2H, m), 7.72-7.75(2H, m), 8.43(1H, d), 8.54(1H, d), 10.15(1H, brs) |
| 2 | 4-Me—Ph | F+: 468<br>N1: 1.98-2.06(4H, m), 2.34(3H, s), 2.68-2.70(1H, m), 2.97-3.02(4H, m), 4.35(2H, s), 7.28 (2H, d), 7.36(2H, d), 7.63-7.66(2H, m), 7.72-7.76(2H, m), 8.43(1H, s), 8.54(1H, s), 10.14(1H, s) |
| 3 | 3-Me—Ph | F+: 468<br>N1: 2.01-2.09(4H, m), 2.35(3H, s), 2.71(1H, m), 2.93-3.0 |

TABLE 4-continued (Ia)

| Ex | A | Dat |
|---|---|---|
|   |   | 6(4H, m), 4.36(2H, s), 7.17-7.38 (4H, m), 7.64(2H, d), 7.73(2H, d), 8.43(1H, d), 8.54(1H, d), 10.15(1H, s) |
| 4 | 2-Me—Ph | F+: 468<br>N1: 1.88-2.15(4H, m), 2.15(3H×0.1, s), 2.26(3H×0.9, s), 2.41-2.46(1H, m), 2.83-3.05(4H, m), 3.86(1H×0.9, d), 4.20(1H×0.1, d), 4.74(1H×0.9, d), 4.84(1H×0.1, d), 7.09-7.77(8H, m), 8.43(1H, d), 8.53(1H, d), 10.14(1H×0.9, s), 10.19(1H×0.1, s) |
| 5 | 2,3-(Me)₂—Ph | F+: 482<br>N1: 1.85-2.12(4H, m), 2.03(3H×0.1, s), 2.15(3H×0.9, s), 2.25(3H×0.1, s), 2.31(3H×0.9, s), 2.42-2.47(1H, m), 2.83-2.90(1H, m), 3.00-3.22(3H, m), 3.84(1H×0.9, d), 4.16(1H×0.1, d), 4.72(1H×0.9, d), 4.84(1H×0.1, d), 7.07-7.36(3H, m), 7.62-7.66(2H, m), 7.71-7.76(2H, m), 8.43(1H, brs), 8.54(1H, d), 10.12(1H×0.9, s), 10.16(1H×0.1, s) |

TABLE 5

| Ex | A | Dat |
|---|---|---|
| 6 | 2.4-(Me)₂—Ph | F+: 482<br>N1: 1.88-2.50(5H, m), 2.09(3H×0.1, s), 2.21(3H×0.9, s), 2.25(3H×0.1, s), 2.30(3H×0.9, s), 2.85-3.20(4H, m), 3.81(1H×0.9, d), 4.17(1H×0.1, d), 4.72(1H×0.9, d), 4.81(1H×0.1, d), 6.97-7.39(3H, m), 7.62-7.66(2H, m), 7.72-7.76(2H, m), 8.43(1H, s), 8.54(1H, s), 10.11(1H×0.9, s), 10.17(1H×0.1, s) |
| 7 | 2,5-(Me)₂—Ph | F+: 482<br>N1: 1.86-2.51(5H, m), 2.08(3H×0.1, s), 2.20(3H×0.9, s), 2.22(3H×0.1, s), 2.30(3H×0.9, s), 2.87-3.26(4H, m), 3.84(1H×0.9, d), 4.21(1H×0.1, d), 4.70(1H×0.9, d), 4.80(1H×0.1, d), 6.92-7.32(3H, m), 7.63-7.65(2H, m), 7.72-7.76(2H, m), 8.43(1H, s), 8.54(1H, s), 10.12(1H×0.9, s), 10.17(1H×0.1, s) |
| 8 | 3,4-(Me)₂—Ph | F+: 482<br>N1: 1.92-2.08(4H, m), 2.09(3H, s), 2.24(3H, s), 2.71(1H, s), 2.94-3.06(4H, m), 4.33(2H, S), 7.17-7.24(3H, m), 7.64(2H, d), 7.73(2H, d), 8.43(1H, s), 8.54(1H, s), 10.12(1H, s) |

TABLE 5-continued

| | | |
|---|---|---|
| 9 | 3,5-(Me)₂—Ph | F+: 482<br>N1: 1.96-2.14(4H, m), 2.30(6H, s), 2.73(1H, m), 2.95-3.04 (4H, m), 4.33(2H, S), 7.02(1H, s), 7.08(2H, s), 7.64(2H, d), 7.73(2H, d), 8.43(1H, s), 8.54(1H, s), 10.12(1H, s) |
| 10 | 2,4,6-(Me)₃—Ph | F+: 496<br>N1: 1.87-2.45(5H, m), 2.08(3H×0.1, s), 2.09(6H×0.1, s), 2.27(3H×0.9, s), 2.28(6H×0.9, s), 3.01-3.26(4H, m), 4.16 (2H×0.9, s), 4.44(2H×0.1, s), 6.88(2H×0.1, s), 7.01 (2H×0.9, s), 7.61-7.65(2H, m), 7.71-7.75(2H, m), 8.43(1H, s), 8.54(1H, s), 10.12(1H×0.9, s), 10.14(1H×0.1, s) |
| 11 | 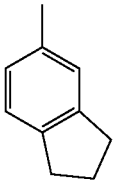 | F+: 494<br>N1: 2.01-2.08(6H, m), 2.70-3.06(9H, m), 4.34(2H, s), 7.13-7.32(3H, m), 7.64(2H, d), 7.73(2H, d), 8.43(1H, s), 8.54 (1H, s), 10.13(1H, s) |

TABLE 6

| | | |
|---|---|---|
| 12 | 3-Cl-4-Me—Ph | F+: 502<br>N1: 2.01-2.06(4H, m), 2.36(3H, s), 2.68-2.75(1H, m), 3.01-3.06(4H, m), 4.37(2H, S), 7.37-7.40(1H, m), 7.46(1H, d), 7.60-7.66(3H, m), 7.74(2H, d), 8.44(1H, s), 8.55(1H, s), 10.18(1H, s) |
| 13 | 4-Cl-3-Me—Ph | F+: 502<br>N1: 2.00-2.06(4H, m), 2.36(3H, s), 2.68-2.75(1H, m), 3.01-3.04(4H, m), 4.36(2H, S), 7.33-7.36(1H, m), 7.48-7.52(2H, m), 7.64(2H, d), 7.73(2H, d), 8.43(1H, s), 8.54(1H, s), 10.18(1H, s) |
| 14 | 3-F-4-Me—Ph | F+: 486<br>N1: 2.00-2.05(4H, m), 2.26(3H, s), 2.70-2.77(1H, m), 3.01-3.03(4H, m), 4.36(2H, S), 7.24-7.26(1H, m), 7.32-7.41(2H, m), 7.64(2H, d), 7.73(2H, d), 8.43(1H, s), 8.54(1H, s), 10.17(1H, s) |
| 15 | 3-Br-4-Me—Ph | F+: 546, 548<br>N1: 2.00-2.06(4H, m), 2.38(3H, s), 2.68-2.74(1H, m), 3.01-3.04(4H, m), 4.36(2H, S), 7.41-7.47(2H, m), 7.64(2H, d), 7.73-7.76(3H, d), 8.43(1H, s), 8.54(1H, s), 10.18(1H, s) |
| 16 | 5-F-2-Me—Ph | F+: 486<br>N1: 1.88-2.15(4H, m), 2.11(3H × 0.1, s), 2.23(3H × 0.9, s), 2.45-2.49(1H, m), 2.96-3.16(4H, m), 3.92(1H × 0.9, d), 4.27(1H × 0.1, d), 4.70(1H × 0.9, d), 4.82(1H × 0.1, d), 6.95-6.98(1H × 0.1, m), 7.06-7.10(1H × 0.1, m), 7.20-7.25(1H × 0.9, m), 7.29-7.33(1H × 0.1, m), 7.37-7.7.40(1H × 0.9, m), 7.42-7.46(1H × 0.9, m), 7.65(2H, d), 7.74(2H, d), 8.43(1H, s), 8.54(1H, s), 10.18(1H × 0.9, s), 10.23(1H × 0.1, s) |
| 17 | 3-F-2,4-(Me)₂—Ph | F+: 500<br>N1: 1.88-2.23(4H, m), 2.03(3H × 0.1, s), 2.16(3H × 0.9, s), 2.20(3H × 0.1, s), 2.26(3H × 0.9, s), 2.47-2.54(1H, m), 2.87-3.17(4H, m), 3.91(1H0.9, d), 4.25(1H × 0.1, d), 4.66(1H × 0.9, d), 4.80(1H × 0.1, d), 6.88(1H × 0.1, dd), 7.10(1H × 0.1, dd), 7.21(1H × 0.9, dd), 7.28(1H × 0.9, dd), 7.64(2H, d), 7.73(2H, s), 8.43(1H, s), 8.54(1H, s), 10.14(1H × 09, s), 10.20(1H × 0.1, s) |

TABLE 7

| | | |
|---|---|---|
| 18 | 4-F-3,5-(Me)₂—Ph | F+: 500<br>N1: 2.00-2.05(4H, m), 2.24(6H, s), 2.67-2.74(1H, m), 3.00-3.04(4H, m), 4.33(2H, S), 7.23(2H, d), 7.65(2H, d), 7.74(2H, d), 8.43(1H, s), 8.54(1H, s), 10.15(1H, s) |
| 19 | 3,5-F₂-4-Me—Ph | F+: 504<br>N1: 1.99-2.05(4H, m), 2.17(3H, s), 2.75-2.82(1H, m), 2.99-3.10(4H, m), 4.37(2H, S), 7.28(2H, d), 7.65(2H, d), 7.74(2H, d), 8.44(1H, s), 8.55(1H, s), 10.21(1H, s) |
| 20 | 2-F-4-Me—Ph | F+: 486<br>N1: 1.89-2.11(4H, m), 2.30(3H × 0.1, s), 2.36(3H × 0.9, s), 2.60-2.68(1H, m), 3.01-3.26(4H, m), 3.94(1H × 0.9, d), 4.02(1H × 0.1, d), 4.50(1H × 0.1, d), 4.76(1H × 0.9, d), 7.00(1H × 0.1, d), 7.09(1H × 0.1, d), 7.12(1H × 0.9, d), 7.24(1H × 0.9, d), 7.38(1H × 0.1, dd), 7.50(1H × 0.9, dd), 7.63(2H, d), 7.73(2H, d), 8.44(1H, s), 8.55(1H, s), 10.17(1H × 0.9, s), 10.23(1H × 0.1, s) |

TABLE 8

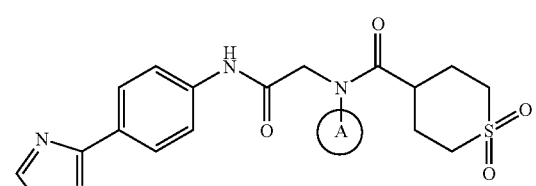

(Ib)

| Ex | A | Dat |
|---|---|---|
| 21 | 4-Me—Ph | F+: 469<br>N1: 1.94-2.11(4H, m), 2.34(3H, s), 2.65-2.75(1H, m), 2.92-3.08(4H, m), 4.38(2H, s), 7.28(2H, d), 7.37(2H, d), 7.79 (2H, d), 8.00(2H, d), 9.66(1H, s), 10.38(1H, s) |
| 22 | 3-Me—Ph | F−: 467<br>N1: 1.96-2.11(4H, m), 2.35(3H, s), 2.65-2.76(1H, m), 2.92-3.09(4H, m), 4.39(2H, s), 7.20-7.39(4H, m), 7.79(2H, d), 8.00(2H, d), 9.66(1H, s), 10.38(1H, s) |
| 23 | 2-Me—Ph | F+: 469<br>N1: 1.88-2.26(4H+3H, m), 2.42-2.52(1H, m), 2.84-3.18(4H, m), 3.91(1H×0.9, d), 4.44(1H×0.1, d), 4.75(1H×0.9, d), 4.87(1H×0.1, d), 7.08-7.54(4H, m), 7.75-7.81(2H, m), 7.97-8.04(2H, m), 9.66(1H×0.9, s), 9.67(1H×0.1, s), 10.37 (1H×0.9, s), 10.41(1H×0.1, s) |

TABLE 8-continued

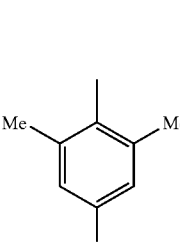

(Ib)

| Ex | A | Dat |
|---|---|---|
| 24 | 2,3-(Me)$_2$—Ph | F-: 481<br>N1: 1.83-2.31(4H+3H+3H, m), 2.42-2.54(1H, m), 2.82-3.16 (4H, m), 3.88(1H×0.9, d), 4.19(1H×0.1, d), 4.72(1H×0.9, d), 4.87(1H×0.1, d), 7.05-7.37(3H, m), 7.75-7.80(2H, m), 7.97-8.03(2H, m), 9.66(1H×0.9, s), 9.66(1H×0.1, s), 10.35(1H×0.9, s), 10.38(1H×0.1, s) |
| 25 | 2,4-(Me)$_2$—Ph | F-: 481<br>N1: 1.84-2.33(4H+3H+3H, m), 2.42-2.52(1H, m), 2.84-3.19 (4H, m), 3.86(1H×0.9, d), 4.21(1H×0.1, d), 4.73(1H×0.9, d), 4.84(1H×0.1, d), 6.95-7.40(3H, m), 7.75-7.81(2H, m), 7.98-8.02(2H, m), 9.66(1H×0.9, s), 9.66(1H×0.1, s), 10.35(1H X0.9, s), 10.39(1H×0.1, s) |

TABLE 9

| 26 | 2,5-(Me)$_2$—Ph | F-: 481<br>N1: 1.84-2.32(4H+3H+3H, m), 2.42-2.52(1H, m), 2.87-3.18 (4H, m), 3.89(1H×0.9, d), 4.25(lH×0.1, d), 4.72(1H×0.9, d), 4.83(1H×0.1, d), 6.92-7.34(3H, m), 7.76-7.82(2H, m), 7.98-8.04(2H, m), 9.66(1H×0.9, s), 9.67(1H×0.1, s), 10.37(1H×0.9, s), 10.39(1H×0.1, s) |
| 27 | 2,6-(Me)$_2$—Ph | F-: 481<br>N1: 1.88-2.42(5H+6H, m), 2.98-3.27(4H, m), 4.22(2H×0.86, s) 4.51(2H×0.14, s), 7.1-7.3(3H, m), 7.76-7.81(2H, m), 7.99-8.03(2H, m), 9.66(1H, s), 10.38(1H, s) |
| 28 | 3,4-(Me)$_2$—Ph | F+: 483<br>N1: 1.97-2.20(4H, m), 2.24(6H, s), 2.67-2.76(1H, m), 2.96-3.30(4H, m), 4.37(2H, s), 7.17-7.27(3H, m), 7.79(2H, d), 8.00(2H, d), 9.66(1H, s), 10.36(1H, s) |
| 29 | 3,5-(Me)$_2$—Ph | F+: 483<br>N1: 1.98-2.12(4H, m), 2.30(6H, s), 2.65-2.78(1H, m), 2.93-3.10(4H, m), 4.36(2H, s), 7.00-7.12(3H, m), 7.79(2H, d), 8.00(2H, d), 9.66(1H, s), 10.37(1H, s) |
| 30 | 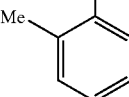 | F-: 495<br>N1: 1.83-2.52(4H+9H+1H, m), 2.99-3.26(4H, m), 4.18(2H×0.9, s), 4.48(2H×0.1, s), 6.88(2H×0.1, s), 7.01(2H×0.9, s), 7.74-7.82(2H, m), 7.94-8.03(2H, m), 9.66(1H, s), 10.36(1H, s) |

TABLE 9-continued

| 31 | 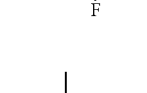 | F-: 499<br>N1: 1.82-2.44(6H+5H, m), 2.98-3.30(4H, m), 4.21(2H×0.85, s), 4.50(2H×0.15, s), 6.95(2H×0.15, d), 7.08(2H×0.85, d), 7.75-7.82(2H, m), 7.97-8.04(2H, m), 9.66(1H×0.85, s), 9.66(1H×0.15, s), i0.40(1H, brs) |
| 32 | 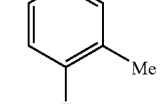 | F+: 487<br>N1: 1.97-2.11(4H, m), 2.26(3H, brs), 2.63-2.74(1H, m), 2.95-3.07(4H, m), 4.38(2H, s), 7.21-7.45(3H, m), 7.79(2H, d), 8.00(2H, d), 9.66(1H, s), 10.39(1H, s) |
| 33 | (indane structure, 5-Me) | F-: 493<br>N1: 1.96-2.20(6H, m), 2.70-2.78(1H, m), 2.84-3.08(8H, m), 4.37(2H, s), 7.04-7.33(3H, m), 7.79(2H, d), 8.00(2H, d), 9.66(1H, s), 10.37(1H, s) |

TABLE 10

| 34 | 4-Me-3-Br—Ph | F-: 546<br>N1: 1.96-2.16(4H, m), 2.38(3H, s), 2.66-2.77(1H, m), 2.96-3.08(4H, m), 4.39(2H, s), 7.40-7.49(2H, m), 7.73-7.82(3H, m), 8.00(2H, d), 9.66(1H, s), 10.41(1H s) |
| 35 | 3-F-4-Me—Ph | F+: 487<br>N1: 1.97-2.07(4H, m), 2.26(3H, s), 2.69-2.77(1H, m), 2.99-3.03(4H, m), 4.39(2H, s), 7.22-7.28(1H, m), 7.31-7.42(2H, m), 7.80(2H, d), 7.99(2H, d), 9.66(1H, s), 10.40(1H, s) |
| 36 | 3-Cl-4-Me—Ph | F+: 503<br>N1: 1.97-2.11(4H, m), 2.36(3H, s), 2.65-2.78(1H, m), 2.97-3.08(4H, m), 4.39(2H, s), 7.39(1H, dd), 7.45(1H, d), 7.60(1H, d), 7.80(2H, d), 7.99(2H, d), 9.65(1H, s), 10.40(1H, s) |
| 37 | 4-Cl-3-Me—Ph | F+: 503<br>N1: 1.95-2.09(4H, m), 2.36(3H, s), 2.65-2.76(1H, m), 2.95-3.07(4H, m), 4.39(2H, s), 7.36(1H, dd), 7.48(1H, d), 7.51(1H, d), 7.80(2H, d), 7.99(2H, d), 9.66(1H, s), 10.40(1H, s) |
| 38 | 4-F-3,5-(Me)$_2$—Ph | F+: 501<br>N1: 1.94-2.12(4H, m), 2.24(6H, s), 2.64-2.74(1H, m), 2.94-3.08(4H, m), 4.35(2H, s), 7.23(2H, d), 7.79(2H, d), 7.99(2H, d), 9.66(1H s), 10.38(1H, s) |
| 39 | 3-F-2,4-(Me)$_2$—Ph | F+: 501<br>N1: 1.84-2.34(4H + 3H + 3H, m), 2.48-2.55(1H, m), 2.85-3.22(4H, m), 3.98(1H × 0.9, d), 4.30(1H × 0.1, d), 4.65(1H × 0.9, d), 4.81(1H × 0.1, d), 7.22(1H, t), 7.27(1H, d), 7.78(2H, d), 7.98(2H, d), 9.66(1H, s), 10.37(1H × 0.9, s), 10.51(1H × 0.1, s) |

TABLE 10-continued

| 40 | 2-F-4-Me—Ph | F+: 487<br>N1: 1.90-2.18(4H, m), 2.30(3H × 0.1, s), 2.36(3H × 0.9, s), 2.62-2.68(1H, m), 3.01-3.23(4H, m), 3.99(1H, d), 4.77(1H, d), 7.13(1H, d), 7.25(1H, d), 7.50(1H, dd), 7.77(2H, d), 7.99(2H, d), 9.66(1H, s), 10.40(1H × 0.9, s), 10.45(1H × 0.1, s) |
|---|---|---|

TABLE 11

| 41 | 4-F—Ph | F−: 471<br>N1: 1.97-2.22(4H, m), 2.61-2.70(1H, m), 2.95-3.30(4H, m), 4.40(2H, s), 7.21-7.35(2H, m), 7.53-7.58(2H, m), 7.78(2H, d), 8.00(2H, d), 9.66(1H, s), 10.40(1H, s) |
|---|---|---|
| 42 | 3-F—Ph | F−: 471<br>N1: 1.96-2.24(4H, m), 2.65-2.80(1H, m), 2.97-3.22(4H, m), 4.43(2H, s), 7.10-7.56(4H, m), 7.80(2H, d), 8.01(2H, d), 9.66(1H, s), 10.44(1H, s) |
| 43 | 3,4-F$_2$—Ph | F−: 489<br>N1: 1.94-2.25(4H, m), 2.65-2.75(1H, m), 2.97-3.30(4H, m), 4.41(2H, s), 7.37-7.69(3H, m), 7.88(2H, d), 8.00(2H, d), 9.66(1H, s), 10.43(1H, s) |
| 44 | 3,5-Cl$_2$—Ph | F−: 522<br>N1: 1.95-2.12(4H, m), 2.66-2.81(1H, m), 2.95-3.20(4H, m), 4.42(2H, s), 7.64(2H, s), 7.70(1H, s), 7.79(2H, d), 8.01(2H, d), 9.66(1H, s), 10.46(1H, s) |
| 45 | 4-Pr—Ph | F+: 497<br>N1: 0.91(3H, t), 1.55-1.66(2H, m), 1.95-2.13(4H, m), 2.59(2H, t), 2.65-2.75(1H, m), 2.90-3.20(4H, m), 4.39(2H, s), 7.29(2H, d), 7.39(2H, d), 7.79(2H, d), 8.00(2H, d), 9.66(1H, s), 10.37(1H, s) |
| 46 | 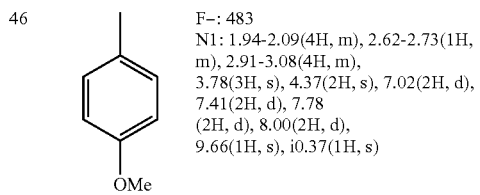 | F−: 483<br>N1: 1.94-2.09(4H, m), 2.62-2.73(1H, m), 2.91-3.08(4H, m), 3.78(3H, s), 4.37(2H, s), 7.02(2H, d), 7.41(2H, d), 7.78(2H, d), 8.00(2H, d), 9.66(1H, s), i0.37(1H, s) |
| 47 | 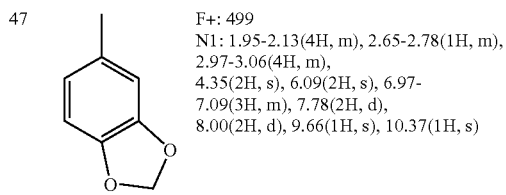 | F+: 499<br>N1: 1.95-2.13(4H, m), 2.65-2.78(1H, m), 2.97-3.06(4H, m), 4.35(2H, s), 6.09(2H, s), 6.97-7.09(3H, m), 7.78(2H, d), 8.00(2H, d), 9.66(1H, s), 10.37(1H, s) |
| 48 | 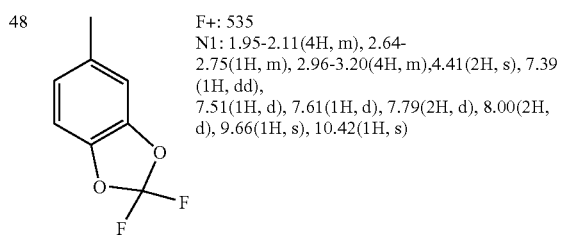 | F+: 535<br>N1: 1.95-2.11(4H, m), 2.64-2.75(1H, m), 2.96-3.20(4H, m), 4.41(2H, s), 7.39(1H, dd), 7.51(1H, d), 7.61(1H, d), 7.79(2H, d), 8.00(2H, d), 9.66(1H, s), 10.42(1H, s) |

TABLE 12

| 49 | 4-F-3-Cl—Ph | F−: 505<br>N1: 1.94-2.30(4H, m), 2.64-2.76(1H, m), 2.92-3.20(4H, m), 4.41(2H, s), 7.46-7.62(2H, m), 7.74-7.83(3H, m), 8.01(2H, d), 9.66(1H, s), 10.44(1H, s) |
|---|---|---|
| 50 | 3-F-2-Me—Ph | F−: 485<br>N1: 1.86-2.22(4H + 3H, m), 2.44-2.54(1H, m), 2.84-3.20(4H, m), 4.03(1H × 0.9, d), 4.34(1H × 0.1, d), 4.67(1H × 0.9, d), 4.83(1H × 0.1, d), 6.98-7.43(3H, m), 7.74-7.82(2H, m), 7.96-8.04(2H, m), 9.65(1H × 0.9, s), 9.65(1H × 0.1, s), 10.38(1H × 0.9, s), 10.42(1H × 0.1, s) |
| 51 | 5-F-2-Me—Ph | F−: 485<br>N1: 1.84-2.24(4H + 3H, m), 2.44-2.52(1H, m), 2.92-3.22(4H, m), 3.99(1H × 0.9, d), 4.33(1H × 0.1, d), 4.69(1H × 0.9, d), 4.81(1H × 0.1, d), 6.93-7.47(3H, m), 7.76-7.81(2H, m), 7.97-8.04(2H, m), 9.66(1H × 0.9, s), 9.66(1H × 0.1, s), 10.40(1H × 0.9, s), 10.43(1H × 0.1, s) |
| 52 | 3,5-(Br)$_2$-4-Me—Ph | F−: 625<br>N1: 1.95-2.10(4H, m), 2.54(3H, s), 2.68-2.82(1H, m), 2.95-3.16(4H, m), 4.40(2H, s), 7.80(2H, d), 7.84(2H, s), 7.99(2H, d), 9.66(1H, s), 10.44(1H, s) |
| 53 | 3,4,5-F$_3$—Ph | F−: 507<br>N1: 1.88-2.12(4H, m), 2.65-2.80(1H, m), 2.95-3.07(4H, m), 4.41(2H, s), 7.48-7.62(2H, m), 7.80(2H, d), 7.99(2H, d), 9.66(1H, s), 10.46(1H, s) |
| 54 | 2,3,5,6-F$_4$-4-Br—Ph | F−: 605<br>N1: 1.90-2.28(4H, m), 2.78-2.88(1H, m), 2.98-3.28(4H, m), 4.46(2H × 0.85, s), 4.70(2H × 0.15, s), 7.72-7.79(2H, m), 7.94-8.03(2H, m), 9.66(1H × 0.85, s), 9.66(1H × 0.15, s), 10.44(1H × 0.85, s), 10.47(1H × 0.15, s) |
| 55 | 3-F-4-MeO—Ph | F−: 501<br>N1: 1.96-2.07(4H, m), 2.65-2.76(1H, m), 2.96-3.06(4H, m), 3.87(3H, s), 4.38(2H, s), 7.21-7.45(3H, m), 7.80(2H, d), 7.99(2H, d), 9.66(1H, s), 10.39(1H, s) |

TABLE 13

| 56 | 3-CF$_3$—4-Cl—Ph | F−: 555<br>N1: 1.94-2.11(4H, m), 2.62-2.76(1H, m), 2.95-3.12(4H, m), 4.46(2H, s), 7.75-7.87(4H, m), 7.97-8.05(3H, m), 9.66(1H, s), 10.47(1H, s) |
|---|---|---|
| 57 | 3-CN-4-Me—Ph | ES+: 494<br>N1: 1.95-2.07(4H, m), 2.52(3H, s), 2.65-2.75(1H, m), 2.98-3.04(4H, m), 4.41(2H, s), 7.58(1H, d), 7.73(1H, dd), 7.79(2H, d), 7.91(1H, d), 7.99(2H, d), 9.66(1H, s), 10.43(1H, s) |
| 58 | 3-CN-4-Cl—Ph | F−: 512<br>N1: 1.94-2.10(4H, m), 2.65-2.80(1H, m), 2.94-3.11(4H, m), 4.44(2H, s), 7.80(2H, d), 7.82-7.92(2H, m), 8.00(2H, d), 8.13(1H, s), 9.66(1H, s), 10.47(1H, s) |
| 59 | 3-Br-4-F—Ph | F+: 553<br>N1: 1.96-2.08(4H, m), 2.63-2.75(1H, m), 2.95-3.10(4H, m), 4.40(2H, s), 7.50(1H, t), 7.55-7.63(1H, m), 7.80(2H, d), 7.91(1H, dd), 7.99(2H, d), 9.66(1H, s), 10.43(1H, s) |

TABLE 13-continued

| | | |
|---|---|---|
| 60 | 3,5-F$_2$-4-Br—Ph | F+: 569<br>N1: 1.92-2.12(4H, m), 2.76-2.90(1H, m), 2.94-3.16(4H, m), 4.43(2H, s), 7.49(2H, d), 7.80(2H, d), 7.99(2H, d), 9.66(1H, s), 10.47(1H, s) |
| 61 | 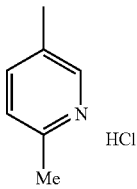 | F−: 468<br>N1: 1.92-2.27(4H, m), 2.64-2.76(3H+1H, m), 2.94-3.38(4H, m), 4.50(2H, s), 7.75-7.90(3H, m), 7.99(2H, d), 8.20-8.40(1H, m), 8.68-8.90(1H, m), 9.57(1H, s), 10.63(1H, s) |
| 62 | 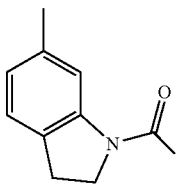 | ES+: 538<br>N1: 1.96-2.18(4H+3H, m), 2.69-2.80(1H, m), 2.96-3.10(4H, m), 3.16(2H, t), 4.14(2H, t), 4.37(2H, s), 7.10(1H, dd), 7.29(1H, d), 7.79(2H, d), 7.98(2H, d), 8.09(1H, d), 9.66(1H, s), 10.39(1H, s) |

TABLE 14

| | | |
|---|---|---|
| 63 | 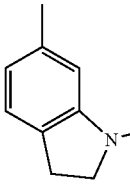 | F+: 554<br>CDCl3: 2.11-2.21 (2H, m), 2.33-2.46(2H, m), 2.75-2.87(3H, m), 3.01(2H, t), 3.16-3.35(4H, m), 3.37(3H, s), 3.50-3.61(4H, m), 4.38(2H, s), 6.36(1H, d), 6.50(1H, dd), 7.02(1H, d), 7.63(2H, d), 8.02(2H, d), 8.66(1H, s), 8.73(1H, s) |
| 64 | 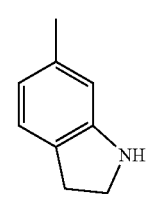 | F−: 494<br>N1: 1.98-2.13(4H, m), 2.73-2.86(1H, m), 2.90-3.12(4H+2H, m), 3.49(2H, t), 4.33(2H, s), 6.59-6.72(2H, m), 7.10(1H, d), 7.80(2H, d), 7.99(2H, d), 9.66(1H, s), 10.36(1H, s) |
| 65 | 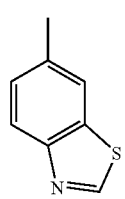 | F−: 510<br>N1: 1.98-2.14(4H, m), 2.69-2.80(1H, m), 2.92-3.04(4H, m), 4.48(2H, s), 7.68(1H, dd), 7.80(2H, d), 8.00(2H, d), 8.18(1H, d), 8.32(1H, d), 9.47(1H, s), 9.66(1H, s), 10.43(1H, s) |

TABLE 14-continued

| | | |
|---|---|---|
| 66 | 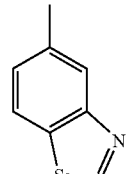 | ESI+: 512<br>N1: 1.99-2.14(4H, m), 2.71-2.80(1H, m), 2.92-3.05(4H, m), 4.50(2H, s), 7.64(1H, dd), 7.80(2H, d), 8.00(2H, d), 8.24(1H, d), 8.28(1H, d), 9.49(1H, s), 9.66(1H, s), 10.43(1H, s) |

TABLE 15

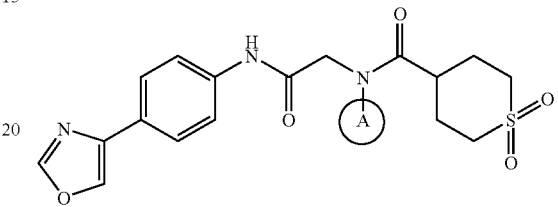

(Ia)

| Ex | A | Dat |
|---|---|---|
| 67 | 4-F—Ph | F+: 472<br>N1: 1.99-2.05(4H, m), 2.62-2.69(1H, m), 2.98-3.02(4H, m), 4.37(2H, s), 7.29-7.34 (2H, m), 7.54-7.57(2H, m), 7.64(2H, d), 7.74(2H, d), 8.43(1H, s), 8.54(1H, s), 10.17(1H, s) |
| 68 | 3,4-F$_2$—Ph | F+: 490<br>N1: 1.99-2.02(4H, m), 2.69(1H, m), 2.98-3.04(4H, m), 4.38 (2H, s), 7.39-7.75 (7H, m), 8.43(1H, s), 8.54(1H, s), 10.20(1H, s) |
| 69 | 3-Me-4-F—Ph | F+: 486<br>N1: 2.00-2.05(4H, m), 2.26(3H, s), 2.64-2.71(1H, m), 2.99-3.03(4H, m), 4.35(2H, s), 7.22-7.44(3H, m), 7.65(2H, d), 7.74(2H, d), 8.43(1H, s), 8.54(1H, s), 10.16(1H, s) |
| 70 | 2-Me-3-F—Ph | F+: 486<br>N1: 1.89-2.20(4H, m), 2.05(3H×0.1, s), 2.18(3H×0.9, s), 2.45-2.51(1H, m), 2.85-3.16(4H, m), 3.96(1H×0.9, d), 4.28(1H×0.1, d), 4.67(1H×0.9, d), 4.84(1H×0.1, d), 6.99-7.41(3H, m), 7.64(2H, d), 7.73(2H, d), 8.43(1H, s), 8.54(1H, s), 10.16(1H×0.9, s), 10.22(1H×0.1, s) |
| 71 | 3,5-Br$_2$-4-Me—Ph | F+: 625<br>N1: 2.00-2.05(4H, m), 2.54(3H, s), 2.70-2.77(1H, m), 3.01-3.12(4H, m), 4.37(2H, s), 7.65(2H, d), 7.74(2H, d), 7.84(2H, s), 8.44(1H, s), 8.55(1H, s), 10.22(1H, s) |
| 72 | 3,4,5-F$_3$—Ph | F+: 508<br>N1: 1.93-2.04(4H, m), 2.71-2.76(1H, m), 3.01-3.08(4H, m 4.38(2H, s), 7.56(2H, dd), 7.65(2H, d), 7.75(2H, d), 8.44(1H, s), 8.55(1H, s), 10.24(1H, s) |

TABLE 16

| | | |
|---|---|---|
| 73 | 3-BnO—Ph | F+: 560<br>N1: 1.95-2.08(4H, m), 2.66-2.74(1H, m), 2.91-3.05(4H, m), |

TABLE 16-continued

| | | |
|---|---|---|
| | | 4.36(2H, s), 5.13(2H, s), 7.07(2H, d), 7.15(1H, s), 7.31-7.47(6H, m), 7.65(2H, d), 7.74(2H, d), 8.43(1H, s), 8.54(1H, s), 10.16(1H, s) |
| 74 | 4-Et—Ph | F+: 482<br>N1: 1.20(3H, t), 1.99-2.09(4H, m), 2.62-2.72(3H, m), 2.94-3.06(4H, m), 4.36(2H, s), 7.31 (2H, d), 7.39(2H, d), 7.64(2H, d), 7.73(2H, d), 8.43(1H, s), 8.54(1H, s), 10.14(1H, s) |
| 75 | 3-CF$_3$-4-Cl—Ph | F+: 556<br>N1: 1.99-2.05(4H, m), 2.65-2.72(1H, m), 3.02-3.06(4H, m), 4.43(2H, s), 7.65(2H, d), 7.74(2H, d), 7.84(2H, s), 8.02(1H, s), 8.43(1H, s), 8.54(1H, s), 10.24(1H, s) |
| 76 | 3-Cl-4-F—Ph | F+: 506<br>N1: 1.99-2.04(4H, m), 2.65-2.72(1H, m), 3.01-3.04(4H, m), 4.38(2H, s), 7.50-7.58(2H, m), 7.65(2H, d), 7.74(2H, d) 7.79-7.81(1H, m), 8.43(1H, s), 8.54(1H, s), 10.20(1H, s) |
| 77 | 3-F-4-MeO—Ph | F+: 502<br>N1: 2.00-2.05(4H, m), 2.67-2.74(1H, m), 3.00-3.03(4H, m), 3.87(3H, s), 4.35(2H, s), 7.22-7.43(3H, m), 7.64(2H, d), 7.74(2H, d), 8.43(1H, s), 8.54(1H, s), 10.16(1H, s) |
| 78 | (methylenedioxyphenyl structure) | F+: 498<br>N1: 2.00-2.06(4H, m), 2.69-2.76(1H, m), 3.01-3.04(4H, m), 4.33(2H, s), 6.09(2H, s), 6.98(2H, s), 7.09(1H, s), 7.64(2H, d), 7.74(2H, d), 8.43(1H, s), 8.54(1H, s), 10.14(1H, s) |

TABLE 17

| | | |
|---|---|---|
| 79 | (difluoromethylenedioxyphenyl structure) | F+: 534<br>N1: 2.00-2.05(4H, m), 2.67-2.74(1H, m), 3.00-3.05(4H, m), 4.38(2H, s), 7.39(1H, dd), 7.49(1H, d), 7.62(1H, d), 7.69(2H, d), 7.74(2H, d), 8.44(1H, s), 8.55(1H, s), 10.19(1H, s) |
| 80 | 3-CN-4-Cl—Ph | F−: 511<br>N1: 1.94-2.16(4H, m), 2.67-2.74(1H, m), 2.98-3.04(4H, m), 4.41(2H, s), 7.65(2H, d), 7.74(2H, d), 7.84-7.90(2H, m), 8.12(1H, s), 8.43(1H, s), 8.55(1H, s), 10.24(1H, s) |
| 81 | 3-CN-4-Me—Ph | F−: 491<br>N1: 2.00-2.04(4H, m), 2.52(3H, s), 2.67-2.71(1H, m), 3.00-3.03(4H, m), 4.38(2H, s), 7.57(1H, d), 7.64(2H, d), 7.73-7.75(3H, m), 7.91(1H, s), 8.43(1H, s), 8.54(1H, s), 10.20(1H, s) |
| 82 | 3-F-4-CF$_3$—Ph | F+: 540<br>N1: 2.00-2.06(4H, m), 2.80-2.83(1H, m), 3.00-3.07(4H, m), 4.46(2H, s), 7.55(1H, s), 7.64-7.76(5H, m), 7.90(1H, dd), 8.44(1H, s), 8.55(1H, s), 10.27(1H, s) |
| 83 | 4-CF$_3$—Ph | F+: 522<br>N1: 2.01-2.07(4H, m), 2.70-2.77(1H, m), 3.00-3.05(4H, m), 4.44(2H, s), 7.64-7.85(6H, m), 7.85(2H, d), 8.44(1H, s), 8.54(1H, s), 10.23(1H, s) |
| 84 | 3,5-F$_2$-4-Br—Ph | F+: 568, 570<br>N1: 1.94-2.08(4H, m), 2.79-2.84(1H, m), 3.01-3.11(4H, m), 4.41(2H, s), 7.49(2H, d), 7.65(2H, d), 7.74(2H, d), 8.44(1H, s), 8.55(1H, s), 10.25(1H, s) |
| 85 | 3-Br-4-F—Ph | F+: 550<br>N1: 2.01-2.04(4H, m), 2.65-2.72(1H, m), 2.98-3.04(4H, m), 4.38(2H, s), 7.49(1H, dd), 7.57-7.61(1H, m), 7.65(2H, d), 7.74(2H, d), 7.91(1H, dd), 8.44(1H, s), 8.55(1H, s), 10.21(1H, s) |
| 86 | (methylbenzothiazole structure) | F−: 509<br>N1: 1.99-2.13(4H, m), 2.68-2.79(1H, m), 2.91-3.05(4H, m), 4.46(2H, s), 7.63-7.77(5H, m), 8.17(1H, d), 8.31(1H, d), 8.43(1H, s), 8.53(1H, s), 9.46(1H, s), 10.19 (1H, s) |

TABLE 18

| | | |
|---|---|---|
| 87 | (methylbenzothiazole structure) | F−: 509<br>N1: 1.99-2.13(4H, m), 2.70-2.79(1H, m), 2.91-3.05(4H, m), 4.47(2H, s), 7.61-7.76(5H, m), 8.21-8.30(2H, m), 8.43(1H, s), 8.54(1H, s), 9.49(1H, s), 10.19(1H, s) |
| 88 | (methylindoline structure) | F−: 493<br>N1: 1.98-2.12(4H, m), 2.76-2.83(1H, m), 2.92(2H, dd), 2.97-3.09(4H, m), 3.46(2H, dd), 4.29(2H, s), 5.75(1H, s), 6.54-6.56(2H, m), 7.05(1H, d), 7.64(2H, d), 7.73(2H, d), 8.43(1H, s), 8.54(1H, s), 10.11(1H, s) |
| 89 | (N-acetyl methylindoline structure) | F+: 537<br>N1: 1.98-2.09(4H, m), 2.16(3H, s), 2.71-2.78(1H, m), 2.96-3.07(4H, m), 3.15(2H, dd), 4.14(2H, dd), 4.34(2H, s), 7.09(1H, d), 7.30(1H, d), 7.64(2H, d), 7.73(2H, d), 8.43(1H, s), 8.54(1H, s), i0.13(1H, s) |
| 90 | 3-OH-4-Me—Ph | F+: 484<br>N1: 1.96-2.09(4H, m), 2.12(3H, m), 2.74-2.78(1H, m), 3.01-3.05(4H, m), 4.32(2H, s), |

TABLE 18-continued

| | | |
|---|---|---|
| | | 6.78(1H, d), 6.91(1H, s), 7.13 (1H, d), 7.65(2H, d), 7.74(2H, d), 8.43(1H, s), 8.54(1H, s), 9.65(1H, s), 10.13(1H, s) |
| 91 | 5-Me-2-Me-phenyl with OCH₂CH₂OMe substituent | F+: 542 N1: 2.02-2.07(4H, m), 2.17(3H, s), 2.73-2.80(1H, m), 3.00-3.04(4H, m), 3.33(3H, s), 3.69(2H, t), 4.11(2H, t), 4.36 (2H, s), 6.97(1H, dd), 7.05(1H, d), 7.22(1H, d), 7.65(2H, d), 7.73(2H, d), 8.43(1H, s), 8.54(1H, s), 10.14(1H, s) |
| 92 | 3-NH₂-4-Me—Ph | F+: 483 N1: 1.98-2.09(4H, m), 2.05(3H, s), 2.76-2.82(1H, m), 2.97-3.08(4H, m), 4.29(2H, s), 5.09(2H, s), 6.51(1H, dd), 6.68(1H, d), 6.97(1H, d), 7.64(2H, d), 7.73(2H, d), 8.43(1H, d), 8.54(1H, d), 10.10(1H, s) |

TABLE 19

| | | |
|---|---|---|
| 93 | 5-Me-2-Me-phenyl with OCH₂CH₂NMe₂ substituent | ESI+: 555 N1: 2.01-2.07(4H, m), 2.16(3H, s), 2.26(6H, s), 2.70(2H, t), 2.74-2.78(1H, m), 3.01-3.04(4H, m), 4.07(2H, t), 4.36(2H, s), 6.96(1H, d), 7.06(1H, s), 7.21(1H, d), 7.64(2H, d), 7.73(2H, d), 8.43(1H, s), 8.54(1H, s), 10.14(1H, s) |
| 94 | 5-Me-2-Me-phenyl with OCH₂CH₂OH substituent | ESI+: 528 N1: 1.96-2.12(4H, m), 2.18(3H, s), 2.72-2.80(1H, m), 2.95-3.08(4H, m), 3.68-3.80(2H, m), 3.94-4.06(2H, t), 4.35(2H, s), 4.85(1H, t), 6.96(1H, d), 7.65(2H, d), 7.74(2H, d), 8.44(1H, s), 8.54(1H, s), 10.14(1H, s) |
| 95 | 5-Me-2-Me-phenyl with NHCH₂CH₂OMe substituent | F+: 541 N1: 2.00-2.10(4H, m), 2.07(3H, s), 2.76-2.82(1H, m), 2.97-3.08(4H, m), 3.24-3.27(2H, m), 3.25(3H, s), 3.49 (2H, t), 4.33(2H, s), 5.01(1H, t), 6.58(1H, d), 6.63(1H, s), 7.02(1H, d), 7.64(2H, d), 7.73(2H, d), 8.43(1H, s), 8.54(1H, s), 10.10(1H, s) |
| 96 | 6-Me-1-methyl-1H-indazol-3-yl | F+: 508 N1: 2.00-2.14(4H, m), 2.74-2.84(1H, m), 2.91-3.05(4H, m), 4.06(3H, s), 4.45(2H, s), 7.23-7.30(1H, m), 7.63-7.70(2H, m), 7.71-7.78(3H, m), 7.84(1H, s), 8.10(1H, s), 8.43(1H, s), 8.54(1H, s), 10.18(1H, s) |
| 97 | 6-Me-1-methylindolin-5-yl | F+: 509 N1: 1.97-2.14(4H, m), 2.70(3H, s), 2.73-2.83(1H, m), 2.89(2H, t), 2.95-3.10(4H, m), 4.32(2H, s), 6.54(1H, d), 6.65(1H, dd), 7.07(1H, d), 7.64(2H, d), 7.73(2H, d), 8.43(1H, d), 8.54(1H, d), 10.11(1H, s) |

TABLE 20

| Ex | Str | Dat |
|---|---|---|
| 98 | N-[4-(2H-1,2,3-triazol-2-yl)phenyl]-2-[N-(2,6-dimethylphenyl)-(1,1-dioxidotetrahydro-2H-thiopyran-4-carboxamido)]acetamide | F+: 482 N1: 1.84-2.44(6H+5H), 2.96-3.30(4H, m), 4.20 (2H×0.85, s), 4.50(2H×0.15, s), 7.06-7.27 (3H, m), 7.73-7.81(2H, m), 7.94-8.01(2H, m), 8.08(2H, br), 10.30(1H, s) |
| 99 | N-[4-(2H-1,2,3-triazol-2-yl)phenyl]-2-[N-(4-methoxyphenyl)-4-fluorobenzamido]acetamide | F+: 446 N1: 3.69(3H, s), 4.61 (2H, s), 6.83(2H, d) 7.04-7.04(6H, m), 7.80 (2H, d), 7.98(2H, d), 8.09 (2H, s), 10.39(1H, s) |

TABLE 20-continued

| Ex | Str | Dat |
|---|---|---|
| 100 | | F+: 473<br>N1: 4.77(2H, s), 7.07(2H, t), 7.34-7.45(3H, m), 7.81(2H, d), 7.95-8.12(6H, m), 9.40(1H, s), 10.46(1H, s) |
| 101 | | F+: 456<br>N1: 4.79(2H, s), 7.29(2H, s), 7.45(1H, d), 7.71 (2H, d), 7.94-8.13(6H, m), 8.45(2H, brs), 9.41(1H, s), 10.50(1H, s) |

TABLE 21

| Ex | Str | Dat |
|---|---|---|
| 102 | | F−: 443<br>N1: 2.30(6H, s), 4.39(2H, s), 7.01-7.16(5H, m), 7.24-7.33(2H, m), 7.84(2H, d), 8.01 (2H, d), 9.67(1H, s), 10.48(1H, s) |
| 103 | | F+: 474<br>N1: 4.79(2H, s), 7.04-7.11(2H, m), 7.34-7.45(3H, m), 7.83(2H, d), 7.98-8.08(4H, m), 9.40 (1H, s), 9.67(1H, s), 10.55(1H, s) |
| 104 | | F+: 444<br>N1: 1.10-1.30(2H, m), 1.33-1.52(2H, m), 1.62-1.76(2H, m), 1.88-2.01(2H, m), 2.24-2.37(3H+ 1H, m), 2.59-2.70(1H, m), 4.36(2H, s), 7.27 (2H, d), 7.34(2H, d), 7.78(2H, d), 7.99(2H, d), 9.66(1H, s), 10.34(1H, s) |

TABLE 21-continued
| Ex | Str | Dat |
|---|---|---|
| 105 | 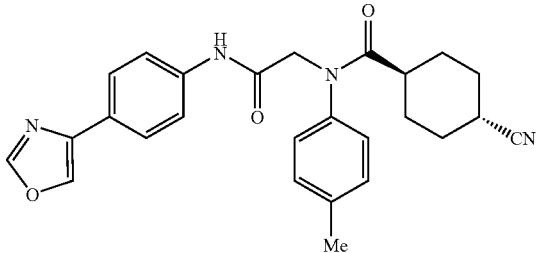 | F+: 443<br>N1: 1.12-1.28(2H, m), 1.34-1.50(2H, m), 1.62-1.74(2H, m), 1.88-2.01 (2H, m), 2.23-2.37(3H+1H, m), 2.59-2.70(1H, m), 4.33(2H, s), 7.27 (2H, d), 7.34(2H, d), 7.64(2H, d), 7.72(2H, d), 8.43(1H, s), 8.54(1H, s), 10.11(1H, s) |
| 106 | 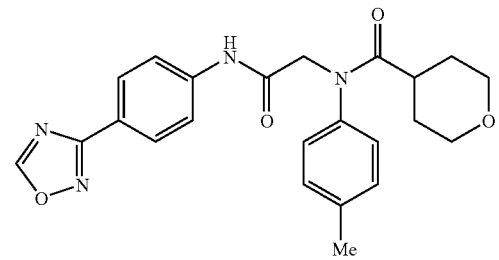 | F+: 421<br>N1: 1.40-1.72(4H, m), 2.34(3H, s), 2.46-2.57 (1H, m), 2.96-3.10(2H, m), 3.70-3.82(2H, m), 4.38(1H, s), 7.27(2H, d), 7.36(2H, d), 7.78 (2H, d), 7.99(2H, d), 9.66(1H, s), 10.35(1H, s) |
| 107 | 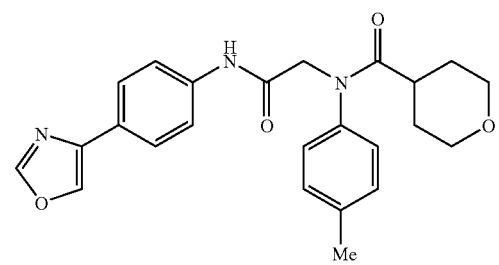 | F+: 420<br>N1: 1.40-1.72(4H, m), 2.33(3H, s), 2.46-2.57 (1H, m), 2.95-3.i0(2H, m), 3.70-3.82(2H, m), 4.35(1H, s), 7.27(2H, d),7.36(2H, d), 7.64(2H, d), 7.73(2H, d),8.43(1H, s), 8.54(1H, s), 10.12(1H, s) |
TABLE 22
| 108 | 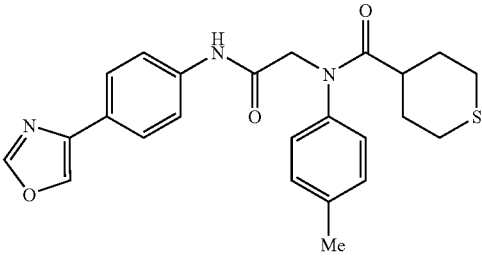 | F−: 450<br>N1: 1.67-1.75(2H, m), 1.95-2.05(2H, m), 2.34(3H, s), 2.40-2.45(2H, m), 2.57(1H, m), 3.17-3.21 (2H, m), 4.46(2H, s), 7.28(2H, d), 7.38(2H, d), 7.64(2H, d), 7.73(2H, d), 8.44(1H, s), 8.54(1H, s), 10.13(1H, s) |
| 109 | 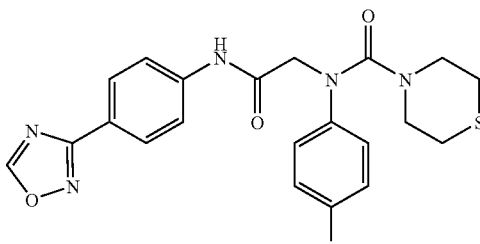 | F+: 438<br>N1: 2.12(3H, s), 2.36-2.43(4H, m), 3.35-3.42(4H, m), 4.39(2H, s), 7.07(2H, d), 7.17(2H, d), 7.80(2H, d), 8.00(2H, d), 9.66(1H, s), 10.35 (1H, s) |

TABLE 22-continued
| 110 | 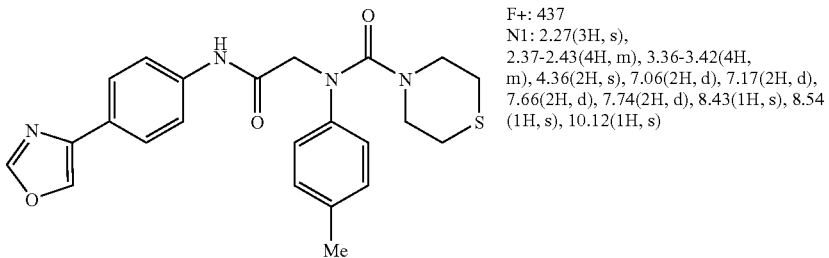 | F+: 437<br>N1: 2.27(3H, s), 2.37-2.43(4H, m), 3.36-3.42(4H, m), 4.36(2H, s), 7.06(2H, d), 7.17(2H, d), 7.66(2H, d), 7.74(2H, d), 8.43(1H, s), 8.54 (1H, s), 10.12(1H, s) |
|---|---|---|
| 111 | 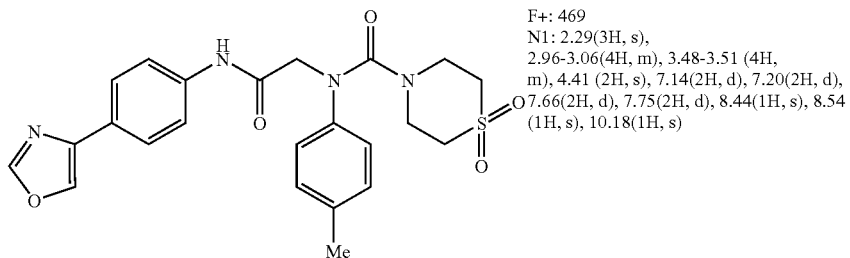 | F+: 469<br>N1: 2.29(3H, s), 2.96-3.06(4H, m), 3.48-3.51 (4H, m), 4.41 (2H, s), 7.14(2H, d), 7.20(2H, d), 7.66(2H, d), 7.75(2H, d), 8.44(1H, s), 8.54 (1H, s), 10.18(1H, s) |
| 112 | 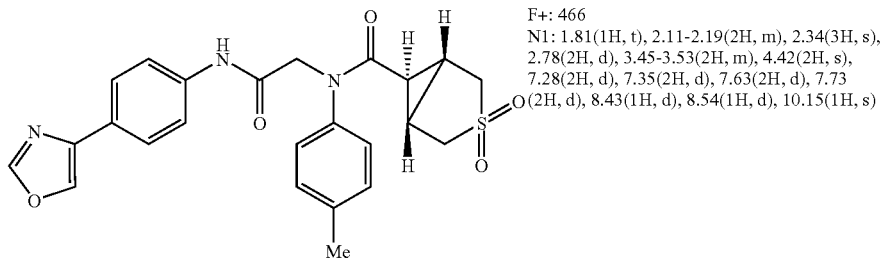 | F+: 466<br>N1: 1.81(1H, t), 2.11-2.19(2H, m), 2.34(3H, s), 2.78(2H, d), 3.45-3.53(2H, m), 4.42(2H, s), 7.28(2H, d), 7.35(2H, d), 7.63(2H, d), 7.73 (2H, d), 8.43(1H, d), 8.54(1H, d), 10.15(1H, s) |
| 113 | 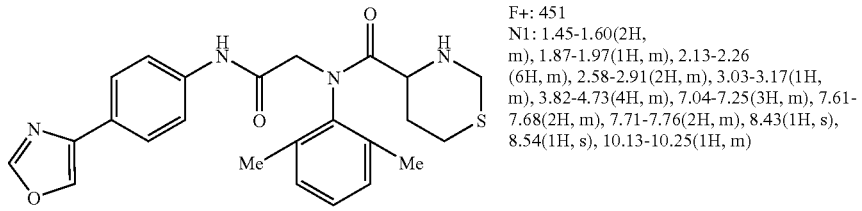 | F+: 451<br>N1: 1.45-1.60(2H, m), 1.87-1.97(1H, m), 2.13-2.26 (6H, m), 2.58-2.91(2H, m), 3.03-3.17(1H, m), 3.82-4.73(4H, m), 7.04-7.25(3H, m), 7.61-7.68(2H, m), 7.71-7.76(2H, m), 8.43(1H, s), 8.54(1H, s), 10.13-10.25(1H, m) |
TABLE 23
| 114 | 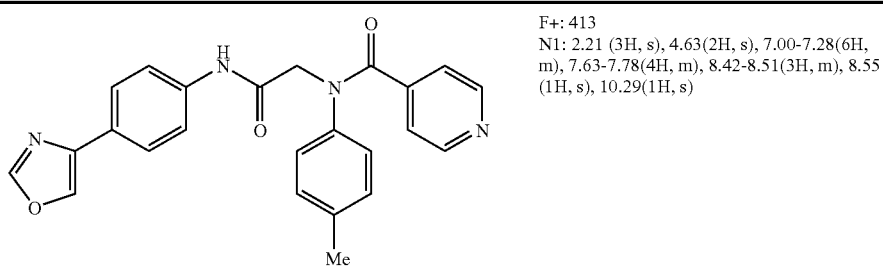 | F+: 413<br>N1: 2.21 (3H, s), 4.63(2H, s), 7.00-7.28(6H, m), 7.63-7.78(4H, m), 8.42-8.51(3H, m), 8.55 (1H, s), 10.29(1H, s) |
|---|---|---|

TABLE 23-continued
| | | |
|---|---|---|
| 115 | 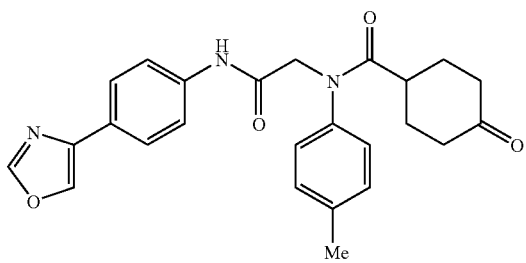 | F+: 432<br>N1: 1.71-1.85(2H, m), 1.88-2.00(2H, m), 2.08-2.25(4H, m), 2.34(3H, s), 2.70-2.80(1H, m), 4.37(2H, s), 7.29(2H, d), 7.41(2H, d), 7.64(2H, d), 7.73(2H, d), 8.43(1H, s), 8.54(1H, s), 10.13(1H, s) |
| 116 | 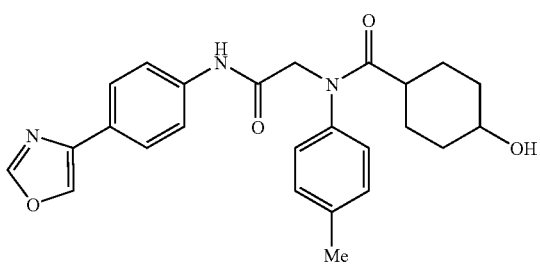 | F+: 434<br>N1: 0.72-0.88(2H, m), 1.05-1.20(1H, m), 1.28-1.48(2H, m), 1.51-1.85(4H, m), 2.08-2.18(1H, m), 2.30-2.36(3H, m), 4.33(2H, s), 7.27(2H, d), 7.34(2H, d), 7.64(2H, d), 7.72(2H, d), 8.43(1H, s), 8.54(1H, s), 10.09(1H, s) |
| 117 | 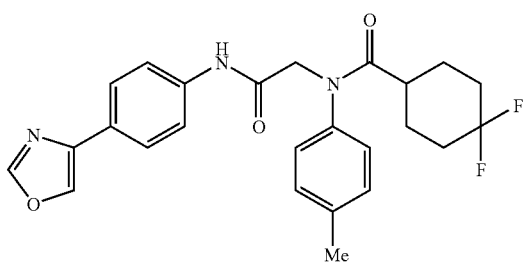 | F+: 454<br>N1: 1.46-1.78(6H, m), 1.90-2.05(2H, m), 2.33(3H, s), 2.37-2.48(1H, m), 4.35(2H, s), 7.27(2H, d), 7.37(2H, d), 7.64(2H, d), 7.73(2H, d), 8.43(1H, s), 8.54(1H, s), 10.12(1H, s) |
| 118 | 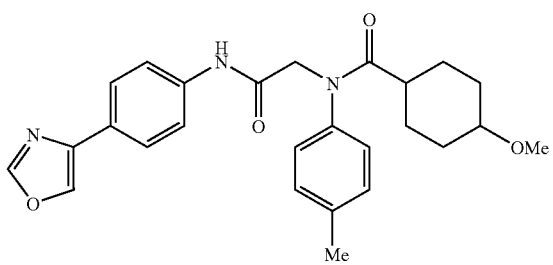 | F+: 448<br>N1: 0.68-0.81(1H, m), 1.02-2.01(7H, m), 2.13-2.32(1H, m), 2.32-2.35(3H, m), 4.33(2H, s), 7.23-7.29(2H, m), 7.34(2H, d), 7.64(2H, d), 7.72(2H, d), 8.43(1H, s), 8.54(1H, s), 10.09(1H, s) |
| 119 | 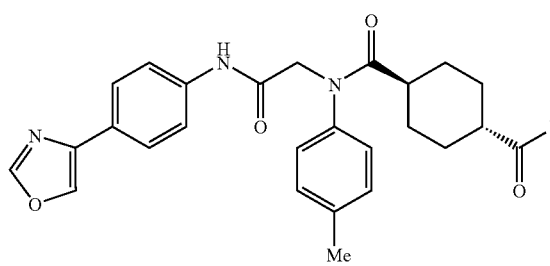 | F+: 461<br>N1: 0.95-1.08(2H, m), 1.30-1.45(2H, m), 1.63-1.75(4H, m), 1.96-2.08(1H, m), 2.14-2.24(1H, m), 2.34(3H, s), 4.35(2H, s), 6.61 (1H, s), 7.15(1H, s), 7.27(2H, d), 7.35(2H, d), 7.64(2H, d), 7.73(2H, d), 8.43(1H, s), 8.54(1H, s), 10.11(1H, s) |

TABLE 24
| 120 | 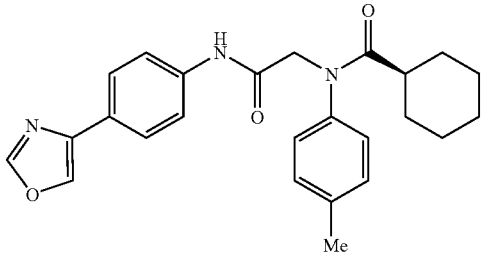 | F+: 448<br>N1: 0.52-0.66(2H, m), 1.20-1.44(3H, m), 1.60-1.74(4H, m), 2.12-2.22(1H, m), 2.33(3H, s), 3.11(2H, t), 4.28(1H, t), 4.34(2H, s) 7.26(2H, d), 7.34(2H, d), 7.64(2H, d), 7.73(2H, d), 8.43(1H, d), 8.54(1H, d), 10.10(1H, s) |
|---|---|---|
| 121 | 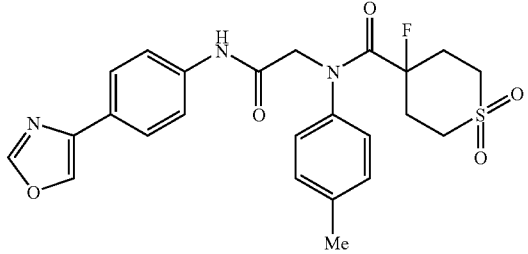 | F+: 486<br>N1: 2.31 (3H, s), 2.34-2.70(4H, m), 3.05-3.15 (4H, m) 4.36(2H, s), 7.20(2H, d), 7.33(2H, d), 7.64(2H, d), 7.74(2H, d), 8.43(1H, s), 8.54(1H, s), 10.16(1H, s) |
| 122 | 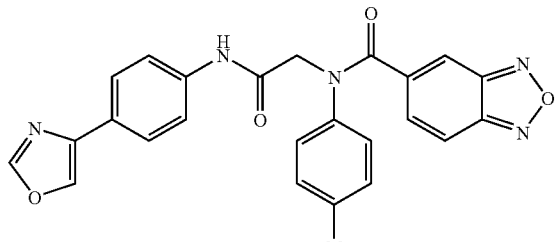 | F+: 454<br>N1: 2.19(3H, s), 4.68(2H, s), 7.08(2H, d), 7.25(2H, d), 7.48(1H, d), 7.65-7.79(4H, m), 7.90-8.04(2H, m), 8.44(1H, s), 8.56(1H, s) |
| 123 | 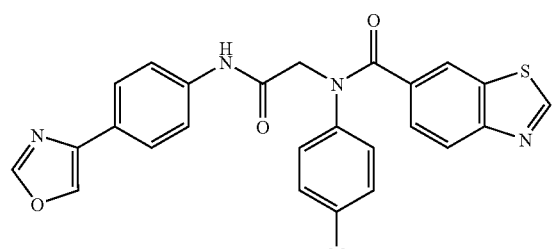 | F+: 469<br>N1: 2.18(3H, s), 4.66(2H, s), 7.04(2H, d), 7.15(2H, d), 7.39(2H, d), 7.69(2H, d), 7.75 (2H, d), 7.90(2H, d), 8.21(1H, s), 8.44(1H, s), 8.56(1H, s), 9.43(1H, s), 10.29(1H, s) |
| 124 | 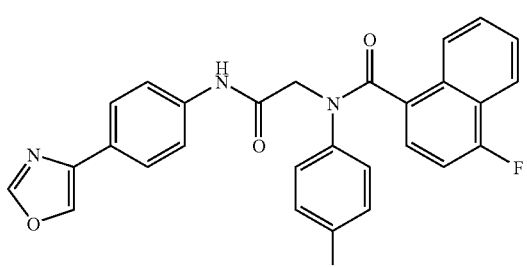 | F+: 480<br>2.08(3H, s), 4.72(2H, s), 6.89(2H, d), 7.08-7.23(3H, m), 7.37-7.43(1H, m), 7.58-7.82 (6H, m), 7.99(1H, d), 8.36(1H, d), 8.45(1H, s), 8.57(1H, s), 10.38(1H, s) |
| 125 | 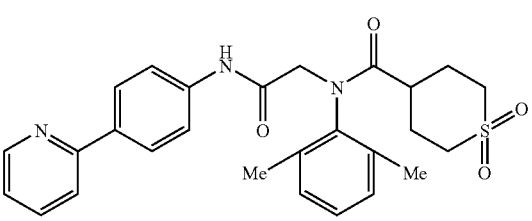 | F+: 492<br>N1: 1.87-2.44(6H+5H, m), 2.97-3.27(4H, m), 4.21(2H×0.85, s), 4.50(2H×0,15, s), 7.07-7.33(4H, m), 7.68-7.73(2H, m), 7.83-7.92(2H, m), 8.05-8.08(2H, m), 8.63-8.6 4(1H, m), 10.22(1H, s) |

TABLE 25

(I)

[Structure: Z-Ph-NH-C(=O)-CH2-N(A)-C(=O)-tetrahydrothiopyran-1,1-dioxide]

| Co | A | Z |
|---|---|---|
| a1 | 4-F—Ph | 2-methyl-2H-1,2,3-triazol-4-yl |
| a2 | 3-F—Ph | |
| a3 | 3,4-F2—Ph | |
| a4 | 3,5-(Cl)2—Ph | |
| a5 | 2,3-Me2—Ph | |
| a6 | 2,5-(Me)2—Ph | |
| a7 | 3,4-(Me)2—Ph | |
| a8 | 2,4,6-(Me)3—Ph | |
| a9 | 4-F-3-Me—Ph | |
| a10 | 3-Br-4-Me—Ph | |
| a11 | 4-Me—Ph | |
| a12 | 3-Me—Ph | |
| a13 | 2-Me—Ph | |
| a14 | 4-Pr—Ph | |
| a15 | 2,4-(Me)2—Ph | |
| a16 | 3,5-(Me)2—Ph | |
| a17 | 4-F-2,6-(Me)2—Ph | |
| a18 | 3-Cl-4-F—Ph | |
| a19 | 6-methyl-2,3-dihydro-1H-indenyl | |
| a20 | 4-Cl-3-Me—Ph | |
| a21 | 2-F-4-Me—Ph | |
| a22 | 3-F-2,4-(Me)2—Ph | |
| a23 | 3-F-4-Me—Ph | |
| a24 | 5-F-2-Me—Ph | |
| a25 | 3,5-F2-4-Me—Ph | |
| b1 | 4-F—Ph | 2-pyridinyl (2-methyl) |
| b2 | 3-F—Ph | |
| b3 | 3,4-F2—Ph | |
| b4 | 3,5-(Cl)2—Ph | |
| b5 | 2,3-(Me)2—Ph | |
| b6 | 2,5-(Me)2—Ph | |
| b7 | 3,4-(Me)2—Ph | |
| b8 | 2,4,6-(Me)3—Ph | |
| b9 | 4-F-3-Me—Ph | |
| b10 | 3-Br-4-Me—Ph | |
| b11 | 4-Me—Ph | |
| b12 | 3-Me—Ph | |
| b13 | 2-Me—Ph | |
| b14 | 4-Pr—Ph | |
| b15 | 2,4-(Me)2—Ph | |
| b16 | 3,5-(Me)2—Ph | |
| b17 | 4-F-2,6-(Me)2—Ph | |
| b18 | 3-Cl-4-F—Ph | |
| b19 | 6-methyl-2,3-dihydro-1H-indenyl | |

TABLE 25-continued (I)

[Structure: Z-Ph-NH-C(=O)-CH2-N(A)-C(=O)-tetrahydrothiopyran-1,1-dioxide]

| Co | A | Z |
|---|---|---|
| b20 | 4-Cl-3-Me—Ph | |
| b21 | 2-F-4-Me—Ph | |
| b22 | 3-F-2,4-(Me)2—Ph | |
| b23 | 3-F-4-Me—Ph | |
| b24 | 5-F-2-Me—Ph | |
| b25 | 3,5-F2-4-Me—Ph | |

TABLE 26

(I)

[Structure: Z-Ph-NH-C(=O)-CH2-N(A)-X-R3]

| Co | Z |
|---|---|
| a26 | [N-methyl-N-(2,6-dimethylphenyl)-4-fluorobenzamide with 2-methyl-2H-1,2,3-triazole] |
| a27 | [N-methyl-N-(4-methylphenyl)-4-cyanocyclohexanecarboxamide] |
| a28 | [N-methyl-N-(4-methylphenyl)-tetrahydrothiopyran-1-oxide-4-carboxamide] |

TABLE 26-continued

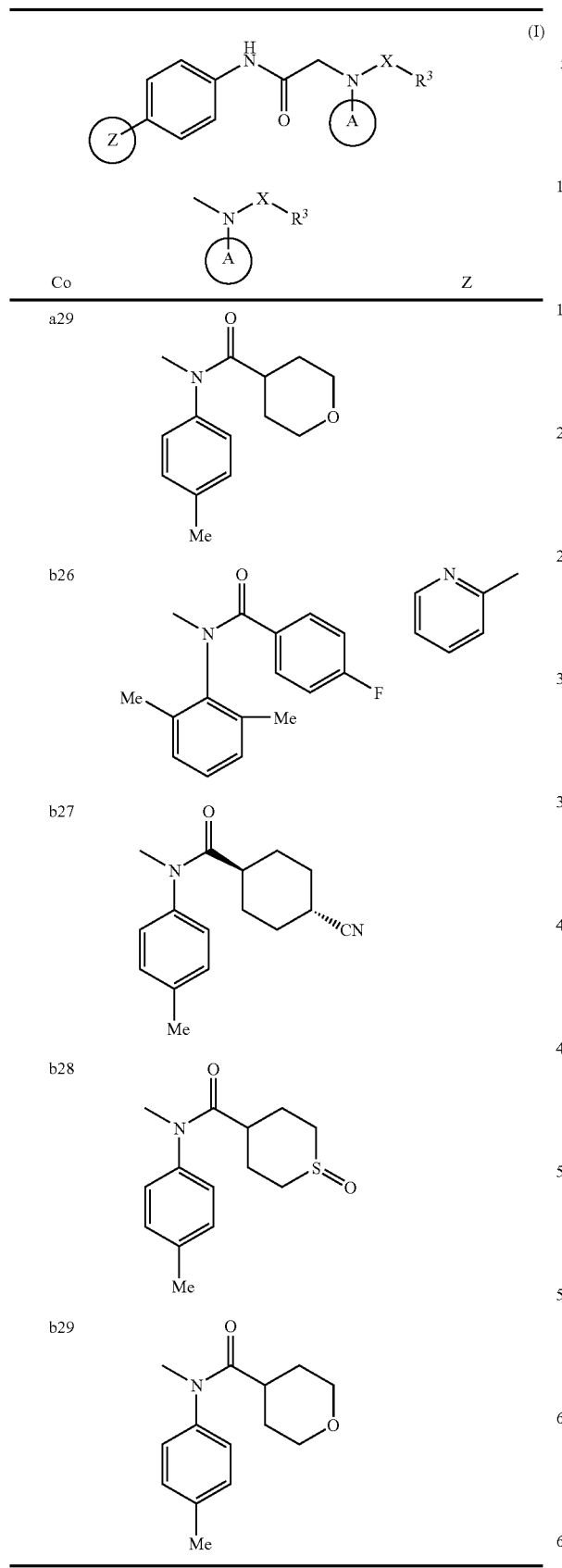

The invention claimed is:

1. An amide derivative of formula (I) or a salt thereof,

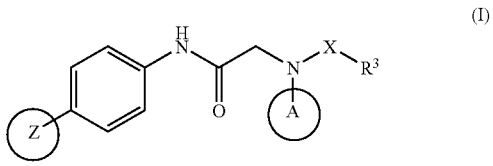

wherein:
Z represents 1,2,4-oxadiazol-3-yl, 4-oxazolyl, 1,2,3-triazol-2yl or 2-pyridyl group;
A represents a substituted or unsubstituted aryl group, a substituted or unsubstituted heteroaryl group, a substituted or unsubstituted saturated hydrocarbon ring-fused aryl group or a substituted or unsubstituted saturated heterocyclic ring-fused aryl group, provided that the saturated hydrocarbon ring-fused aryl or saturated heterocyclic ring-fused aryl group is bonded to a nitrogen atom via a carbon atom in an aromatic ring;
X represents -CO- or -S(O)$_2$-;
$R^3$ represents a substituted or unsubstituted alkyl, a substituted or unsubstituted alkenyl, a substituted or unsubstituted alkenyl, a substituted or unsubstituted cycloalkyl, a substituted or unsubstituted cycloalkenyl, a substituted or unsubstituted aryl, or a substituted or unsubstituted heterocyclic group, or $NR_aR_b$; and
$R_a$ and $R_b$ are the same or different from each other and represents H, a lower alkyl, lower alkenyl, lower alkenyl, cycloalkyl, cycloalkenyl, aryl, 5- or 6-membered monocyclic heteroaryl which has 1 to 4 hetero atoms selected from a group consisting of N, S and O, or lower alkylenearyl group.

2. The amide derivative or a salt thereof according to claim 1, wherein X is -CO- and wherein Z, A, $R^3$, $R_a$ and $R_b$ have the meanings recited in claim 1.

3. The amide derivative or a salt thereof according to claim 1, wherein A is an aryl group selected from a phenyl and naphthyl group; a heteroaryl group selected from a pyridyl, pyrimidinyl, benzofuranyl, benzothienyl, benzothiadiazolyl, benzothiazolyl, benzoxazolyl, benzoxadiazolyl, benzimidazolyl, indolyl, isoindolyl, indazolyl, imidazopyridyl and indolidinyl group; a saturated hydrocarbon ring-fused aryl group selected from 4-indanyl, 5-indanyl, 5,6,7,8-tetrahydronaphthalene-1-yl and 5,6,7,8- tetrahydronaphthalene-2-yl; or a saturated heterocyclic ring-fused aryl group selected from a 3, 4-dihydro-2H-1,4-benzoxadinyl, 3,4-dihydro-2H-1,4-benzothiadinyl, 1,3-benzodioxolyl, 2, 3-dihydro-1,4benzodioxynyl, chromanyl, isochromanyl, 3,4-dihydro-2H-1-benzothiopyranyl, 3, 4-dihydro-1H-2-benzothiopyranyl, indolinyl, isoindolinyl, 1,2,3,4-tetrahydroquinolyl, and 1,2,3, 4-tetrahydroisoquinolyl group; the aryl, heteroaryl, saturated hydrocarbon ring-fused aryl and saturated heterocyclic ring-fused aryl each may have 1 to 5 substituents selected from Group D1;

$R^3$ is a cycloalkyl selected from cyclopentyl, cyclohexyl and cycloheptyl, cycloalkenyl selected from cyclopentenyl and cyclohexenyl, aryl selected from phenyl and naphthyl, saturated heterocyclic ring-fused aryl selected from 1,3-benzodioxolyl, 2,3-dihydro-1, 4-benzodioxinyl, 3,4-dihydro-2H-1-benzothiopyranyl and 3,4-dihydro-1H-2benzothiopyranyl, heteroaryl selected from pyridyl, pyrimidinyl, benzofuranyl, benzothienyl, benzothiadiazolyl, benzothiazolyl, benzoxazolyl, benzoxadiazolyl, benzimidazolyl, indolyl, isoindolyl, indazolyl, imidazopyridyl and indolidinyl group, or 5- to 8-membered saturated heterocyclic group selected from tetrahydro-2Hpyranyl, tetrahydro-2H-thiopyranyl, thiepanyl, thiabicyclo[3.1.0]hexanyl, perhydro-1,3-thiazinyl, pyrrolidinyl, imidazolidinyl, pyrazolidinyl, piperadinyl, azepanyl, diazepanyl, piperidinyl, morpholinyl and thiomorpholinyl group, the cycloalkyl, cycloalkenyl, aryl, saturated heterocyclic ring-fused aryl, heteroaryl and 5- to 8-membered saturated heterocyclic group each may have 1 to 5 substituents selected from Group D1 and the sulfur atom of the ring may form oxide or dioxide; and Group D1 is a lower alkyl, phenyl, halogeno lower alkyl, COOH, COO-lower alkyl, CO-lower alkyl, halogen atoms, $NO_2$, CN, OH, lower alkylene-OH, lower alkylene-O-lower alkyl, O-lower alkyl, O-halogeno lower alkyl, O-lower alkylene-OH, O-lower alkylene-O-lower alkyl, O-lower alkylene-COOH, O-lower alkylene-COO-lower alkyl, O-lower alkylene-$NH_2$, O-lower alkylene-NH-lower alkyl, O-lower alkylene-N(lower alkyl)$_2$, O-lower alkylene-(a nitrogen-containing saturated heterocyclic group which may be substituted with a lower alkyl group(s)), O-phenyl, O-lower alkylene-phenyl, $NH_2$, NH-lower alkyl, NH-lower alkylene-OH, NH-lower alkylene-O-lower alkyl, NH-lower alkylene-$NH_2$, NH-lower alkylene-NH-lower alkyl, NH-lower alkylene-N(lower alkyl)$_2$, NH-lower alkylene-(a nitrogen-containing saturated heterocyclic group which may be substituted with a lower alkyl group(s)), N(lower alkyl)$_2$, (a nitrogen-containing saturated heterocyclic group which may have a substituent(s) selected from lower alkyl and lower alkylene-COORa), NHCO-lower alkyl, N(lower alkyl)CO-lower alkyl, $CONH_2$, CONH-lower alkyl, CON(lower alkyl)$_2$, =O(oxo), SH, S-lower alkyl, SO-lower alkyl, and $SO_2$-lower alkyl; and wherein Z, X, $R_a$ and $R_b$ have the meanings recited in Claim 1.

4. The amide derivative or a salt thereof according to claim 1, wherein A is a group selected from a phenyl, pyridyl, benzothiazolyl, indazolyl, 5-indanyl, 1,3-benzodioxolyl and indolinyl group, all of which may have 1 to 3 substituents selected from a group consisting of a lower alkyl, lower alkylene-O-lower alkyl, $CF_3$, halogen atoms, CO-lower alkyl, OH, O-lower alkyl, CN, $OCF_3$, O-lower alkylene-OH, O-lower alkylene-O-lower alkyl, $NH_2$, NH-lower alkyl, N(lower alkyl)2, NH-lower alkylene-OH, NH-lower alkylene-O-lower alkyl and O-lower alkylene-phenyl; and $R^3$ is a group selected from a cyclohexyl, phenyl, naphthyl, pyridyl, pyrimidinyl, benzothiazolyl, benzooxadiazolyl, thiabicyclo[3.1.0]hexanyl, tetrahydro-2H-pyranyl, thiomorpholinyl, tetrahydro-2H-thiopyranyl and perhydro-1,3-thiazinyl group, all of which may be substituted with 1 or 2 substituents selected from halogen atoms, CN, =O, OH, O-lower alkyl, lower alkylene-OH and $CONH_2$ and the sulfur atom of the ring may form oxide or dioxide; and wherein Z, X, $R_a$ and $R_b$ have the meanings recited in claim 1.

5. The amide derivative or a salt thereof according to claim 1, wherein Z is 1,2,4-oxadiazol-3-yl group and wherein A, X, $R^3$, $R_a$ and $R_b$ have the meanings recited in claim 1.

6. The amide derivative or a salt thereof according to claim 1, wherein Z is 4-oxazolyl group and wherein A, X, $R^3$, $R_a$ and $R^b$ have the meanings recited in claim 1.

7. The amide derivative or a salt thereof according to claim 1, wherein A is a group selected from a phenyl and 5-indanyl group, all of which may have 1 to 4 substituents selected from a group consisting of a lower alkyl, O-lower alkyl and halogen atoms; X is -CO-; and $R^3$ is 1,1-dioxidotetrahydro-2H-thiopyran-4-yl; and wherein Z, $R_a$ and $R_b$ have the meanings recited in claim 1.

8. The amide derivative or a salt thereof according to claim 7, wherein A is a phenyl, which is substituted with a methyl group and may further have 1 or 2 substituents selected from a group consisting of methyl and halogen atoms.

9. The amide derivative or a salt thereof according to claim 7, wherein A is 5-indanyl group.

10. A pharmaceutical composition which comprises the amide derivative or a salt thereof according to claim 1 and a pharmaceutically acceptable carrier.

11. A method of treating herpes virus infection, which comprises administering to a patient in need of such treatment a therapeutically effective amount of an amide derivative or a salt thereof according to claim 1.

* * * * *